United States Patent
Mazanec

(10) Patent No.: US 11,806,531 B2
(45) Date of Patent: Nov. 7, 2023

(54) IMPLANTABLE COCHLEAR SYSTEM WITH INNER EAR SENSOR

(71) Applicant: Envoy Medical Corporation, White Bear Lake, MN (US)

(72) Inventor: Paul R. Mazanec, Ham Lake, MN (US)

(73) Assignee: Envoy Medical Corporation, White Bear Lake, MN (US)

( * ) Notice: Subject to any disclaimer, the term of this patent is extended or adjusted under 35 U.S.C. 154(b) by 130 days.

(21) Appl. No.: 17/109,303

(22) Filed: Dec. 2, 2020

(65) Prior Publication Data
US 2022/0168569 A1 Jun. 2, 2022

(51) Int. Cl.
*A61N 1/36* (2006.01)
*A61N 1/05* (2006.01)
(Continued)

(52) U.S. Cl.
CPC ....... *A61N 1/36038* (2017.08); *A61N 1/0541* (2013.01); *A61N 1/37235* (2013.01);
(Continued)

(58) Field of Classification Search
CPC .............. A61N 1/0541; A61N 1/36038; A61N 1/36039
See application file for complete search history.

(56) References Cited

U.S. PATENT DOCUMENTS 2,827,041 A  3/1958  Pierson
4,400,590 A  8/1983  Michelson
(Continued)

FOREIGN PATENT DOCUMENTS

CN  104394930 A  3/2015
CN  110086237 A  8/2019
(Continued)

OTHER PUBLICATIONS

Mazanec et al., unpublished U.S. Appl. No. 17/006,467, entitled Programming of Cochlear Implant Accessories, filed Aug. 28, 2020, 74 pages.
(Continued)

*Primary Examiner* — George R Evanisko
(74) *Attorney, Agent, or Firm* — Fredrikson & Byron, P.A.

(57) ABSTRACT

Cochlear implant systems can include an inner ear sensor configured to receive a stimulus signal from the cochlear tissue of a wearer and generate an input signal based on the received stimulus signal. The inner ear sensor can be configured to detect pressure, for example, within a wearer's cochlear tissue and generate an input signal based on the detected pressure. The inner ear sensor can be integrated with a cochlear electrode implanted in the cochlear tissue. Systems can include a signal processor programmed with a transfer function and configured to receive an input signal and output a stimulation signal based on the received input signal and transfer function. Systems can include an implantable battery and/or communication module in communication with the signal processor. The implantable battery and/or communication module can be configured to interface with and update the transfer function of the signal processor.

24 Claims, 11 Drawing Sheets

(51) Int. Cl.
*A61N 1/372* (2006.01)
*H04R 25/00* (2006.01)

(52) U.S. Cl.
CPC .......... *H04R 25/30* (2013.01); *H04R 25/556* (2013.01); *H04R 25/602* (2013.01)

(56) References Cited

U.S. PATENT DOCUMENTS

| | | | |
|---|---|---|---|
| 4,495,384 A | 1/1985 | Scott et al. | |
| 4,729,366 A | 3/1988 | Schaefer | |
| 4,850,962 A | 7/1989 | Schaefer | |
| 4,918,745 A | 4/1990 | Hutchison | |
| 5,540,095 A | 7/1996 | Sherman et al. | |
| 5,762,583 A | 6/1998 | Adams et al. | |
| 6,195,585 B1 * | 2/2001 | Karunasiri | A61N 1/37211 607/57 |
| 6,212,431 B1 | 4/2001 | Hahn et al. | |
| 6,259,951 B1 | 7/2001 | Kuzma et al. | |
| 6,272,382 B1 | 8/2001 | Faltys et al. | |
| 6,308,101 B1 | 10/2001 | Faltys et al. | |
| 6,358,281 B1 | 3/2002 | Berrang et al. | |
| 7,225,028 B2 | 5/2007 | Della Santina et al. | |
| 7,319,906 B2 | 1/2008 | Kuzma et al. | |
| 7,376,563 B2 * | 5/2008 | Leysieffer | H04R 25/507 704/271 |
| 7,524,278 B2 | 4/2009 | Madsen et al. | |
| 7,864,968 B2 | 1/2011 | Kulkarni et al. | |
| 7,899,543 B2 | 3/2011 | Hartley et al. | |
| 8,554,329 B1 | 10/2013 | Mann et al. | |
| 8,655,449 B2 | 2/2014 | Haller et al. | |
| 8,679,031 B2 | 3/2014 | Volckaerts | |
| 8,977,369 B1 | 3/2015 | Haller et al. | |
| 9,205,272 B2 | 12/2015 | Suaning et al. | |
| 9,504,076 B2 | 11/2016 | El-Hoiydi et al. | |
| 9,539,430 B2 | 1/2017 | Mishra et al. | |
| 9,555,243 B2 | 1/2017 | Pontoppidan et al. | |
| 9,716,952 B2 | 7/2017 | Mauger | |
| 9,769,558 B2 | 9/2017 | Chandramohan et al. | |
| 9,999,770 B2 | 6/2018 | Walraevens et al. | |
| 10,015,603 B2 | 7/2018 | Sabin | |
| 10,187,792 B2 | 1/2019 | Meskens | |
| 10,292,644 B2 | 5/2019 | Heasman et al. | |
| 10,306,472 B2 | 5/2019 | Battiwalla et al. | |
| 10,342,976 B2 | 7/2019 | Chen et al. | |
| 10,357,656 B2 | 7/2019 | Heasman | |
| 10,560,789 B2 | 2/2020 | Koka et al. | |
| 10,668,284 B2 | 6/2020 | Koka et al. | |
| 10,713,936 B2 | 7/2020 | Banna et al. | |
| 10,772,563 B2 | 9/2020 | Shah et al. | |
| 10,994,127 B2 | 5/2021 | Smith | |
| 11,272,297 B2 | 3/2022 | Waldmann et al. | |
| 11,305,109 B2 | 4/2022 | Heasman et al. | |
| 11,317,842 B2 | 5/2022 | Koka et al. | |
| 2002/0039425 A1 | 4/2002 | Burnett et al. | |
| 2002/0099421 A1 | 7/2002 | Goldsmith et al. | |
| 2004/0230254 A1 | 11/2004 | Harrison et al. | |
| 2005/0033384 A1 | 2/2005 | Sacha | |
| 2005/0197677 A1 | 9/2005 | Stevenson | |
| 2006/0122664 A1 | 6/2006 | Sacha et al. | |
| 2006/0183965 A1 | 8/2006 | Kasic, II et al. | |
| 2008/0195179 A1 | 8/2008 | Quick | |
| 2008/0300658 A1 | 12/2008 | Meskens | |
| 2009/0018616 A1 | 1/2009 | Quick et al. | |
| 2009/0082831 A1 | 3/2009 | Paul et al. | |
| 2009/0187233 A1 | 7/2009 | Stracener | |
| 2009/0192565 A1 | 7/2009 | Lee et al. | |
| 2010/0030012 A1 | 2/2010 | Meskens | |
| 2010/0042183 A1 | 2/2010 | Beck | |
| 2010/0317913 A1 | 12/2010 | Conn et al. | |
| 2011/0082521 A1 | 4/2011 | Botros et al. | |
| 2011/0116669 A1 | 5/2011 | Karunasir | |
| 2011/0137180 A1 | 6/2011 | Johnson et al. | |
| 2011/0144719 A1 | 6/2011 | Perkins et al. | |
| 2011/0160808 A1 | 6/2011 | Lyden et al. | |
| 2011/0280426 A1 | 11/2011 | Bachler | |
| 2011/0295331 A1 | 12/2011 | Wells et al. | |
| 2012/0063610 A1 | 3/2012 | Kaulberg et al. | |
| 2012/0215285 A1 | 8/2012 | Tahmasian et al. | |
| 2012/0277835 A1 | 11/2012 | Della Santina et al. | |
| 2013/0018216 A1 | 1/2013 | Beckerle et al. | |
| 2013/0023953 A1 | 1/2013 | van den Honert | |
| 2013/0193914 A1 | 8/2013 | Gaddam et al. | |
| 2013/0223664 A1 | 8/2013 | Meskens et al. | |
| 2013/0238055 A1 | 9/2013 | Marnfeldt et al. | |
| 2013/0268025 A1 | 10/2013 | Ranu | |
| 2013/0278226 A1 | 10/2013 | Cong et al. | |
| 2013/0317584 A1 | 11/2013 | Stevenson et al. | |
| 2014/0058482 A1 | 2/2014 | Gupta et al. | |
| 2014/0155947 A1 | 6/2014 | Kroll et al. | |
| 2014/0247954 A1 | 9/2014 | Hall et al. | |
| 2014/0270211 A1 | 9/2014 | Solum et al. | |
| 2014/0275730 A1 | 9/2014 | Lievens et al. | |
| 2014/0309712 A1 | 10/2014 | Masaki et al. | |
| 2014/0350652 A1 | 11/2014 | Suwito | |
| 2015/0125012 A1 | 5/2015 | Sabin | |
| 2015/0174416 A1 | 6/2015 | Angara et al. | |
| 2015/0224312 A1 | 8/2015 | Platz et al. | |
| 2015/0256945 A1 | 9/2015 | Mazanec | |
| 2015/0374988 A1 | 12/2015 | Laudanski | |
| 2015/0375003 A1 | 12/2015 | Meskens | |
| 2016/0050760 A1 | 2/2016 | Liao et al. | |
| 2016/0227333 A1 | 8/2016 | Babico | |
| 2017/0043162 A1 | 2/2017 | Lopez-Poveda | |
| 2017/0077938 A1 | 3/2017 | Heubi | |
| 2017/0094396 A1 | 3/2017 | Chandramohan et al. | |
| 2017/0161449 A1 | 6/2017 | Meskens | |
| 2017/0259072 A1 | 9/2017 | Newham et al. | |
| 2017/0360364 A1 | 12/2017 | Heasman et al. | |
| 2018/0028811 A1 | 2/2018 | Van Gerwen et al. | |
| 2018/0028827 A1 | 2/2018 | Schilling et al. | |
| 2018/0041848 A1 | 2/2018 | Nielsen et al. | |
| 2018/0050197 A1 | 2/2018 | Mazanec et al. | |
| 2018/0050198 A1 | 2/2018 | Mazanec et al. | |
| 2018/0050203 A1 | 2/2018 | Mazanec et al. | |
| 2018/0059870 A1 | 3/2018 | Krah | |
| 2018/0264269 A1 | 9/2018 | Meadows | |
| 2018/0317027 A1 | 11/2018 | Bolner et al. | |
| 2018/0333577 A1 | 11/2018 | Nygard et al. | |
| 2018/0361151 A1 | 12/2018 | Ridler et al. | |
| 2019/0045308 A1 | 2/2019 | Chen et al. | |
| 2019/0046116 A1 * | 2/2019 | Shah | A61N 1/0541 |
| 2019/0344073 A1 | 11/2019 | Baker et al. | |
| 2020/0054877 A1 | 2/2020 | Calixto et al. | |
| 2020/0238075 A1 | 7/2020 | Mazanec et al. | |
| 2020/0269034 A1 | 8/2020 | Mazanec et al. | |
| 2020/0269035 A1 | 8/2020 | Mazanec et al. | |
| 2020/0269047 A1 | 8/2020 | Mazanec et al. | |
| 2020/0269048 A1 | 8/2020 | Mazanec et al. | |
| 2020/0269057 A1 | 8/2020 | Mazanec et al. | |
| 2020/0269058 A1 * | 8/2020 | Mazanec | A61N 1/025 |
| 2021/0084417 A1 | 3/2021 | Bagazov et al. | |
| 2021/0135704 A1 | 5/2021 | El-Hoiydi et al. | |
| 2021/0187293 A1 | 6/2021 | Friedling | |
| 2021/0361194 A1 | 11/2021 | Arab et al. | |
| 2022/0339445 A1 | 10/2022 | Litvak et al. | |

FOREIGN PATENT DOCUMENTS

| | | |
|---|---|---|
| DE | 4419070 A1 | 12/1994 |
| DE | 60107062 T2 | 11/2005 |
| DE | 102013214049 B4 | 3/2015 |
| EP | 1043914 A2 | 10/2000 |
| EP | 1683544 B1 | 11/2010 |
| EP | 2884766 B1 | 2/2018 |
| EP | 3120579 B1 | 2/2020 |
| TW | 201142830 A | 12/2011 |
| WO | 2007137032 A2 | 11/2007 |
| WO | 2010056768 A1 | 5/2010 |
| WO | 2014037888 A1 | 3/2014 |
| WO | 2015077773 A1 | 5/2015 |
| WO | 2016122606 A1 | 8/2016 |
| WO | 2017100866 A1 | 6/2017 |

(56) References Cited

FOREIGN PATENT DOCUMENTS

| | | |
|---|---|---|
| WO | 2018035329 A1 | 2/2018 |
| WO | 2018144732 A1 | 8/2018 |
| WO | 2020172500 A1 | 8/2020 |

OTHER PUBLICATIONS

PCT International Search Report and Written Opinion dated Mar. 9, 2022 for related International Application No. PCT/US2021/060712, 11 pages.

* cited by examiner

IMPLANTABLE COCHLEAR SYSTEM WITH INNER EAR SENSOR

BACKGROUND

A cochlear implant is an electronic device that may be at least partially implanted surgically into the cochlea, the hearing organ of the inner ear, to provide improved hearing to a patient. Cochlear implants may include components that are worn externally by the patient and components that are implanted internally in the patient.

External components may include a microphone, a processor, and a transmitter. Cochlear implants may detect sounds via an ear level microphone that conveys these sounds to a wearable processor. Some processors may be worn behind the patient's ear. An electronic signal from the processor may be sent to a transmission coil worn externally behind the ear over the implant. The transmission coil may send a signal to the implant receiver, located under the patient's scalp.

Internal components may include a receiver and one or more electrodes. Some cochlear implants may include additional processing circuitry among the internal components. The receiver may direct signals to one or more electrodes that have been implanted within the cochlea. The responses to these signals may then be conveyed along the auditory nerve to the cortex of the brain where they are interpreted as sound.

Some cochlear implants may be fully implanted and include a mechanism for measuring sound similar to a microphone, signal processing electronics, and means for directing signals to one or more electrodes implanted within the cochlea.

Internal components of such cochlear implant systems typically require electrical power to operate. Thus, a power supply is typically included along with the other internal components. However, performance of such power supplies often degrades over time, and the power supply may require replacement. Additionally, processing circuitry technology continues to advance quickly. Improvements to processing technology over time may render the processing technology in the implanted processing circuitry outdated. Thus, there may be times when it is advantageous to replace/upgrade the processing circuitry.

However, such replacement procedures can be difficult. The location of the implanted internal components is not the most amenable to surgical procedures and tends not to fully heal after many incisions. Additionally, replacement of some components, such as a signal processor, can require removing and reintroducing components such as electrical leads into the patient's cochlear tissue, which can be damaging to the tissue and negatively impact the efficacy of cochlear stimulation.

Additionally, different challenges exist for communicating electrical signals through a patient's body. For example, safety standards can limit the amount of current that can safely flow through a patient's body (particularly DC current). Additionally, the patient's body can act as an undesired signal path between different components within the body (e.g., via contact with the housing or "can" of each component). This can lead to reduced signal strength and/or undesired communication or interference between components. In some cases, electrical signals may even stimulate undesired regions of the patient's cochlear tissue, interfering with the efficacy of the cochlear implant.

SUMMARY

Some aspects of the disclosure are generally directed toward cochlear implant systems. Such systems can include a cochlear electrode, a stimulator in electrical communication with the cochlear electrode, an input source, and a signal processor. The signal processor can be configured to receive an input signal from the input source and output a stimulation signal to the stimulator based on the received input signal and a transfer function of the signal processor.

In some examples, the input source can include an inner ear sensor. The inner ear sensor can be configured to interface, for example, with the cochlear tissue of the wearer and output a signal based on detected signals. In some examples, the inner ear sensor comprises a pressure transducer configured to output a signal representative of pressure detected within the tissue. In some examples, the inner ear sensor can be integrated into the cochlear electrode such that the cochlear electrode and input source can be implanted simultaneously.

In some examples, systems can include one or more processing stages for processing input signals received from the inner ear sensor. In some embodiments, systems can include an analog processing stage and a digital processing. The analog processing stage can be configured to receive an input signal from the inner ear sensor and process the received input signal to generate an analog processed signal. The digital processing stage can be configured to receive the analog processed signal and generate a digitally processed signal. In some such examples, the digital processed signal can correspond to a normalized stimulus signal having reduced gain variability across a range of frequencies and compensating for variability in frequency response of the inner ear sensor. The system can be configured to output a stimulation signal based on the digitally processed signal and a signal processor transfer function.

In some examples, systems can include an implantable battery and/or communication module in communication with a signal processor and configured to provide electrical power to the signal processor. Systems can further include an external hub including a speaker and a wireless communication interface configured to communicate wirelessly with the implantable battery and/or communication module. The external hub can be configured to output a predetermined acoustic signal via the speaker and communicate information regarding the predetermined acoustic signal to the implantable battery and/or communication module via the wireless communication interface.

In some embodiments, the system can be configured to analyze information received from the external hub regarding the output predetermined acoustic signal and the information received from the signal processor representative of the received input signal. The system can determine a relationship between the predetermined acoustic signal output from the speaker of the external hub and the resulting input signal generated via the inner ear sensor. The system can be configured to update a transfer function of the signal processor in response to the determined relationship.

DETAILED DESCRIPTION

Figure 1:
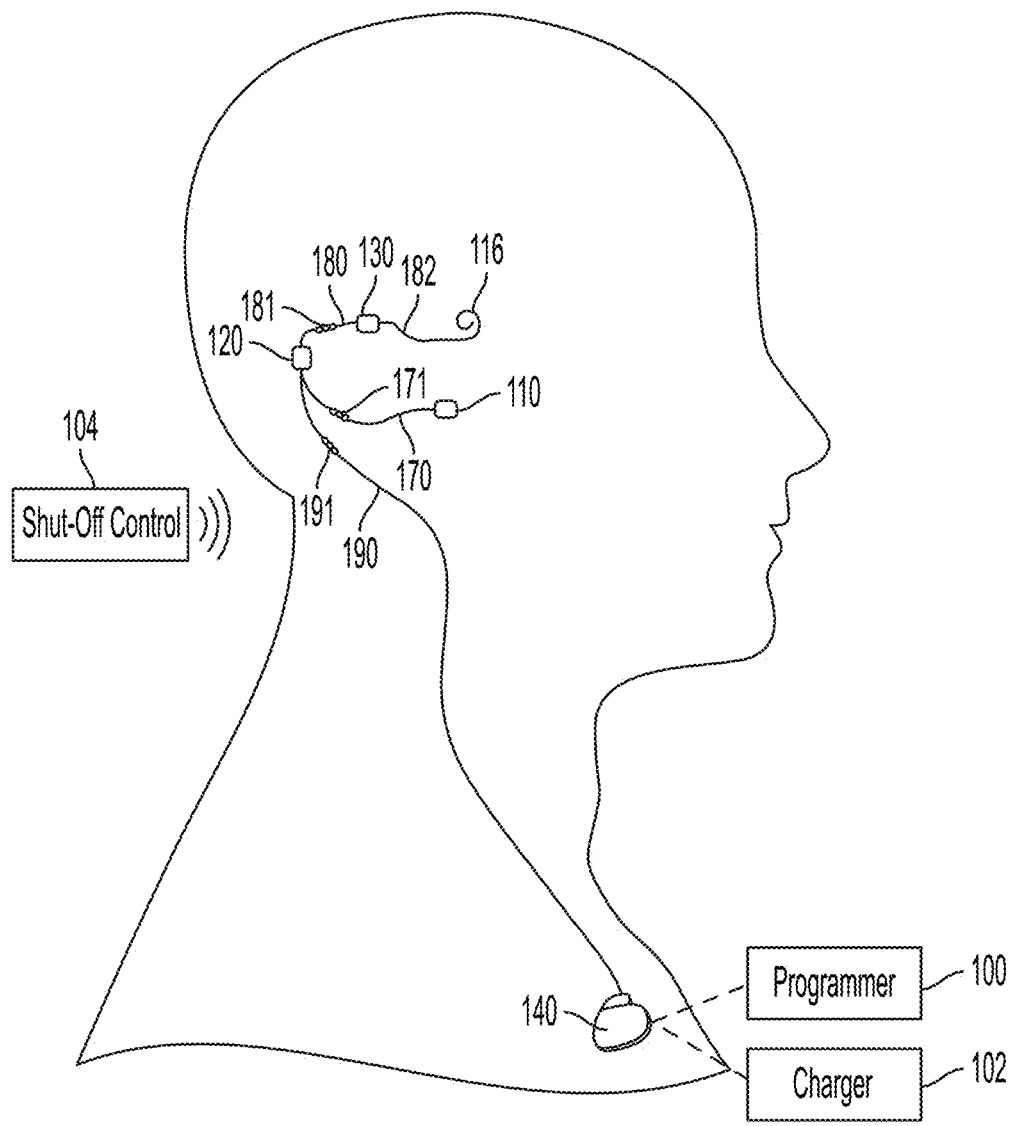
FIG. 1 shows a schematic illustration of a fully implantable cochlear implant system.

FIG. 1 shows a schematic illustration of a fully implantable cochlear implant system. The system of FIG. 1 includes an inner ear sensor 110 in communication with a signal processor 120. The inner ear sensor 110 can be configured to determine information associated with incoming sound waves, for example, by measuring a stimulus in the wearer's cochlear tissue or other inner ear structure. In some examples, the inner ear sensor is configured to sense pressure within the wearer's cochlear tissue and output an electrical signal based on the sensed pressure. For example, in some embodiments, inner ear sensor 110 comprises a transducer configured to output one or more electrical signals based on a sensed pressure.

In some examples, the signal processor 120 can be configured to receive a signal from the inner ear sensor 110 and produce an output signal based thereon. For example, the signal processor 120 can be programmed with instructions to output a certain signal based on a received signal. In some embodiments, the output of the signal processor 120 can be calculated using an equation based on received input signals. Alternatively, in some embodiments, the output of the signal processor 120 can be based on a lookup table or other programmed (e.g., in memory) correspondence between the input signal from the inner ear sensor 110 and the output signal. While not necessarily based explicitly on a function, the relationship between the input to the signal processor 120 (e.g., from the inner ear sensor 110) and the output of the signal processor 120 is referred to as the transfer function of the signal processor 120.

In various examples, the signal processor 120 can comprise any variety of components, for example, digital and/or analog processing components. In some embodiments, signal processor 120 comprises a digital signal processor, one or more microprocessors, microcontrollers, application specific integrated circuits (ASICs) or the like. Supporting circuitry for one or more such components can also be included as a part of the signal processor. In some embodiments, the signal processor can include or otherwise communicate with a memory containing programming for operating one or more components. Additionally or alternatively, in some embodiments, the signal processor can include one or more additional components. For example, in some embodiments, signal processor can include an embedded microphone or other sensor configured to detect incoming sound waves.

The system of FIG. 1 further includes a cochlear electrode 116 implanted into the cochlear tissues of a patient. The cochlear electrode 116 is in electrical communication with an electrical stimulator 130, which can be configured to provide electrical signals to the cochlear electrode 116 in response to input signals received by the electrical stimulator 130. In some examples, the cochlear electrode 116 is fixedly attached to the electrical stimulator 130. In other examples, the cochlear electrode 116 is removably attached to the electrical stimulator 130. As shown, the electrical stimulator 130 is in communication with the signal processor 120. In some embodiments, the electrical stimulator 130 provides electrical signals to the cochlear electrode 116 based on output signals from the signal processor 120.

In various embodiments, the cochlear electrode 116 can include any number of contact electrodes in electrical contact with different parts of the cochlear tissue. In such embodiments, the electrical stimulator 130 can be configured to provide electrical signals to any number of such contact electrodes to stimulate the cochlear tissue. For example, in some embodiments, the electrical stimulator 130 is configured to activate different contact electrodes or combinations of contact electrodes of the cochlear electrode 116 in response to different input signals received from the signal processor 120. This can help the patient differentiate between different input signals.

During exemplary operation, the inner ear sensor 110 detects audio signals, for example, using various features of the wearer's anatomy. The signal processor 120 can receive such signals from the inner ear sensor 110 and produce an output to the electrical stimulator 130 based on the transfer function of the signal processor 120. In some examples, the interface between the signal processor 120 and the inner ear sensor 110 is similar to the interface between a signal processor and middle ear sensor described in PCT Patent Application No. PCT/US20/19166, filed Feb. 21, 2020, and assigned to the assignee of the instant application and which is incorporated herein by reference in its entirety. The electrical stimulator 130 can then stimulate one or more contact electrodes of the cochlear electrode 116 based on the received signals from the signal processor 120.

Figure 2:
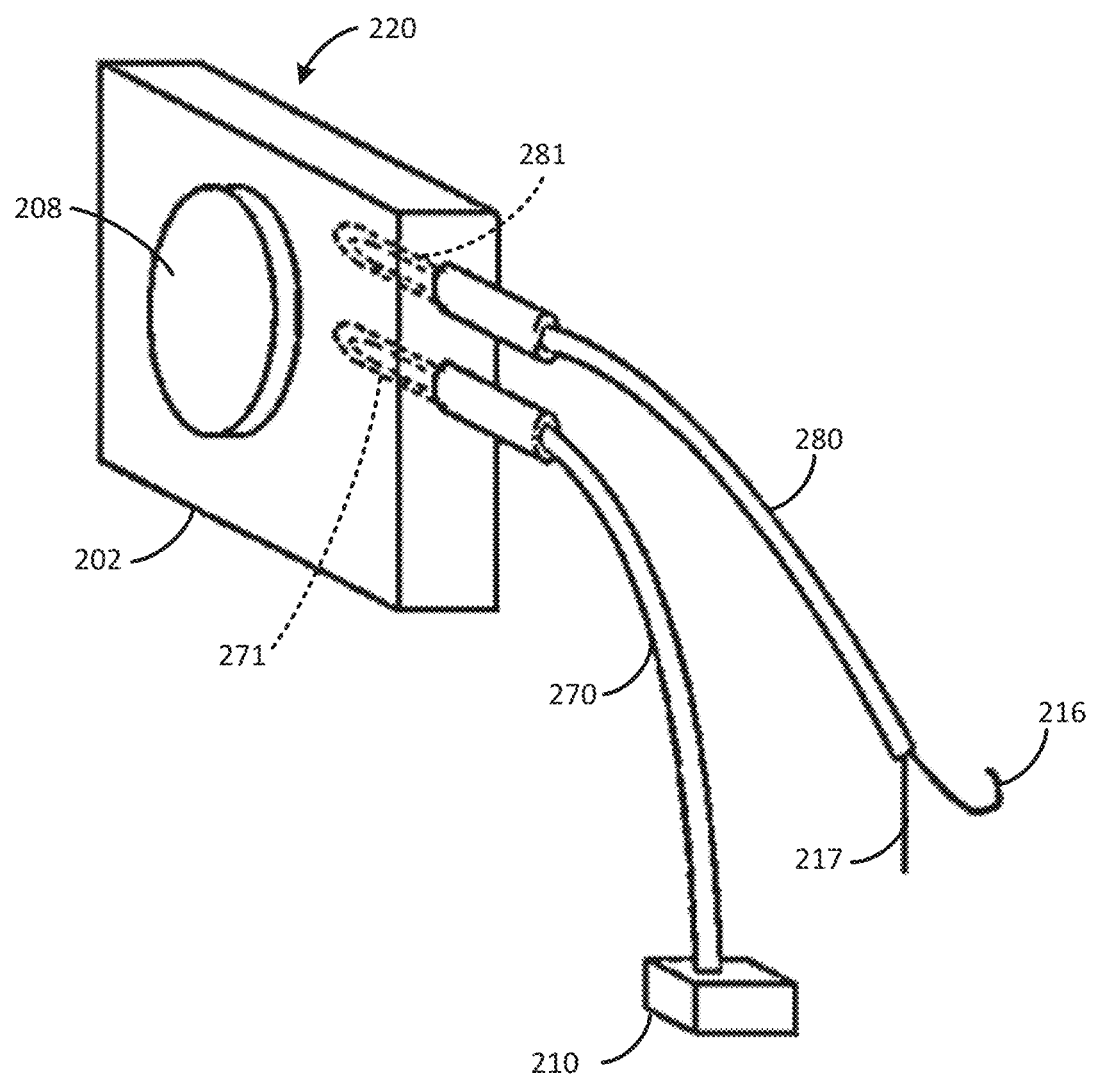
FIG. 2 shows an embodiment of a fully-implantable cochlear implant.

Referring to FIG. 2, an embodiment of a fully-implantable cochlear implant is shown. The device in this embodiment includes a processor 220 (e.g., signal processor), a sensor 210, a first lead 270 connecting the sensor 210 to the processor 220, and a combination lead 280 attached to the processor 220, wherein combination lead 280 contains both a ground electrode 217 and a cochlear electrode 216. The illustrated processor 220 includes a housing 202, a coil 208, first female receptacle 271 and second female receptacle 281 for insertion of the leads 270 and 280, respectively.

In some embodiments, coil 208 can receive power and/or data from an external device, for instance, including a transmission coil (not shown). Some such examples are described in PCT Patent Application No. PCT/US20/19166, which is incorporated by reference. Additionally or alternatively, the processor 220 is configured to receive power and/or data from other sources, such as an implantable battery and/or communication module as shown in FIG. 1. In some examples, such battery and/or communication module can be implanted, for example, into the pectoral region of the patient in order to provide adequate room for larger equipment (e.g., a relatively large battery) for prolonged operation (e.g., longer battery life). Additionally, in the event a battery needs eventual replacement, a replacement procedure in the patient's pectoral region can be performed several times without certain vascularization issues that can arise near the location of the cochlear implant. For example, in some cases, repeated procedures (e.g., battery replacement) near the cochlear implant can result in a decreased ability for the skin in the region to heal after a procedure. Placing a replaceable component such as a battery in the pectoral region can facilitate replacement procedures with reduced risk for such issues.

Figure 3A:
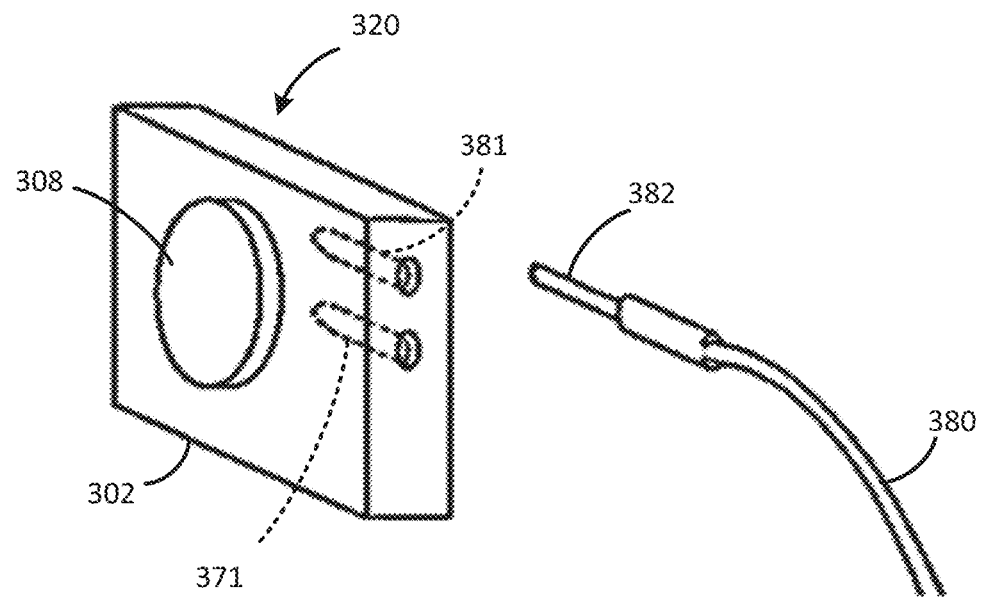
FIGS. 3A and 3B are exemplary illustrations showing communication with a signal processor.
Figure 3B:
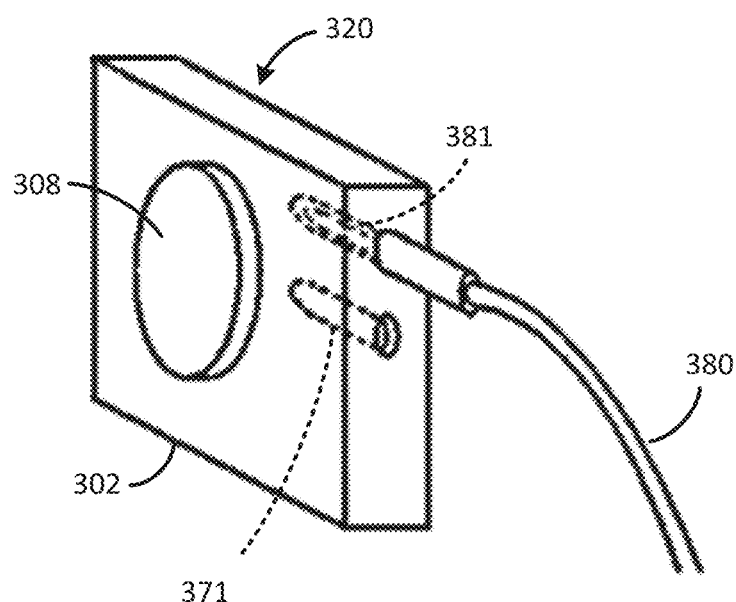

FIGS. 3A and 3B are exemplary illustrations showing communication with a signal processor. For example, referring to FIGS. 3A and 3B, the processor 320, includes a housing 302, a coil 308, and a generic lead 380 are shown. The lead 380 is removable and can be attached to the processor 320 by insertion of a male connector 382 of the generic lead 380 into any available female receptacle, shown here as 371 or 381. FIG. 3A shows the processor 320 with the generic lead 380 removed. FIG. 3B shows the processor 320 with the generic lead 380 attached. The male connector 382 is exchangeable, and acts as a seal to prevent or minimize fluid transfer into the processor 320.

Referring back to FIG. 1, the signal processor 120 is shown as being in communication with the inner ear sensor 110, the electrical stimulator 130, and the implantable battery and/or communication module 140. As described elsewhere herein, the signal processor 120 can receive input signals from the inner ear sensor 110 and/or other input source(s) and output signals to the electrical stimulator 130 for stimulating the cochlear electrode 116. The signal processor 120 can receive data (e.g., processing data establishing or updating the transfer function of the signal processor 120) and/or power from the implantable battery and/or communication module 140. In some embodiments, the signal processor 120 can communicate with such components via inputs such as those shown described PCT Patent Application No. PCT/US20/19166, which is incorporated by reference.

In some embodiments, the implantable battery and/or communication module 140 can communicate with external components, such as a programmer 100 and/or a battery charger 102. The battery charger 102 can wirelessly charge the battery in the implantable battery and/or communication module 140 when brought into proximity with the implantable battery and/or communication module 140 in the pectoral region of the patient. Such charging can be accomplished, for example, using inductive charging. The programmer 100 can be configured to wirelessly communicate with the implantable battery and/or communication module 140 via any appropriate wireless communication technology, such as Bluetooth, Wi-Fi, and the like. In some examples, the programmer 100 can be used to update the system firmware and/or software. In an exemplary operation, the programmer 100 can be used to communicate an updated signal processor 120 transfer function to the implantable battery and/or communication module 140. In various embodiments, the programmer 100 and charger 102 can be separate devices or can be integrated into a single device.

In the illustrated example of FIG. 1, the signal processor 120 is connected to the inner ear sensor 110 via lead 170. In some embodiments, lead 170 can provide communication between the signal processor 120 and the inner ear sensor 110. In some embodiments, lead 170 can include a plurality of isolated conductors providing a plurality of communication channels between the inner ear sensor 110 and the signal processor 120. The lead 170 can include a coating such as an electrically insulating sheath to minimize any conduction of electrical signals to the body of the patient.

In various embodiments, one or more communication leads can be detachable such that communication between two components can be disconnected in order to electrically and/or mechanically separate such components. For instance, in some embodiments, lead 170 includes a detachable connector 171. Detachable connector 171 can facilitate decoupling of the signal processor 120 and inner ear sensor 110, such as described in PCT Patent Application No. PCT/US20/19166, which is incorporated by reference. For example, with reference to FIG. 1, in some embodiments, lead 170 can include a first lead extending from the inner ear sensor 110 having one of a male or a female connector and a second lead extending from the signal processor 120 having the other of the male or female connector. The first and second leads can be connected at detachable connector 171 in order to facilitate communication between the inner ear sensor 110 and the signal processor 120.

In other examples, a part of the detachable connector 171 can be integrated into one of the inner ear sensor 110 and the signal processor 120. For example, in an exemplary embodiment, the signal processor 120 can include a female connector integrated into a housing of the signal processor 120. Lead 170 can extend fully from the inner ear sensor 110 and terminate at a corresponding male connector for inserting into the female connector of the signal processor 120. In still further embodiments, a lead (e.g., 170) can include connectors on each end configured to detachably connect with connectors integrated into each of the components in communication. For example, lead 170 can include two male connectors, two female connectors, or one male and one female connector for detachably connecting with corresponding connectors integral to the inner ear sensor 110 and the signal processor 120. Thus, lead 170 may include two or more detachable connectors.

Similar communication configurations can be established for detachable connector 181 of lead 180 facilitating communication between the signal processor 120 and the stimulator 130 and for detachable connector 191 of lead 190 facilitating communication between the signal processor 120 and the implantable battery and/or communication module 140. Leads (170, 180, 190) can include pairs of leads having corresponding connectors extending from each piece of communicating equipment, or connectors can be built in to any one or more communicating components.

In such configurations, each of the electrical stimulator 130, signal processor 120, inner ear sensor 110, and battery and/or communication module can each be enclosed in a housing, such as a hermetically sealed housing comprising biocompatible materials. Such components can include feedthroughs providing communication to internal components enclosed in the housing. Feedthroughs can provide electrical communication to the component via leads extending from the housing and/or connectors integrated into the components.

In a modular configuration such as that shown in FIG. 1, various components can be accessed (e.g., for upgrades, repair, replacement, etc.) individually from other components. For example, as signal processor 120 technology improves (e.g., improvements in size, processing speed, power consumption, etc.), the signal processor 120 implanted as part of the system can be removed and replaced independently of other components. This can reduce, among other things, the risk, complexity, duration, and recovery time of such a procedure. In some examples, the cochlear electrode 116 can be left in place in the patient's cochlea while other system components can be adjusted, reducing trauma to the patient's cochlear tissue.

While various components are described herein and shown as being detachable, in various embodiments, one or more components configured to communicate with one another can be integrated into a single housing. For example, in some embodiments, signal processor 120 can be integrally formed with the stimulator 130 and cochlear electrode 116. For example, in an exemplary embodiment, processing and stimulation circuitry of a signal processor 120 and stimulator 130 can be integrally formed as a single unit in a housing coupled to a cochlear electrode. Cochlear electrode and the signal processor/stimulator can be implanted during an initial procedure and operate as a single unit.

In some embodiments, while the integral signal processor/stimulator/cochlear electrode component does not get removed from a patient due to potential damage to the cochlear tissue into which the cochlear electrode is implanted, system upgrades are still possible. For example, in some embodiments, a module signal processor may be implanted alongside the integral signal processor/stimulator component and communicate therewith. In some such examples, the integral signal processor may include a built-in bypass to allow a later-implanted signal processor to interface directly with the stimulator. Additionally or alternatively, the modular signal processor can communicate with the integral signal processor, which may be programmed with a unity transfer function. Thus, in some such embodiments, signals from the modular signal processor may be essentially passed through the integral signal processor unchanged so that the modular signal processor effectively controls action of the integral stimulator. Thus, in various embodiments, hardware and/or software solutions exist for upgrading an integrally attached signal processor that may be difficult or dangerous to remove.

Modular systems provide distinct advantages over previous implantable or partially implantable cochlear implant systems. Generally, previous systems include several components included into a single housing implanted into the patient. For example, functionality of a signal processor, electrical stimulator, and sensor can be enclosed in a single, complex component. If any such aspects of the component fail, which becomes more likely as the complexity increases, the entire module must be replaced. By contrast, in a modular system, such as shown in FIG. 1, individual components can be replaced while leaving others in place. Additionally, such systems including, for example, coil-to-coil power and/or data communication through the patient's skin also generally communicate less efficiently than an internal connection such as via the lead 190. Modular systems such as shown in FIG. 1 also allow for a smooth transition from a partially implantable system for a patient who is not yet fully developed and a fully implantable system once the patient has become fully developed. Additional advantages and examples of modular systems are described in PCT Patent Application No. PCT/US20/19166, which is incorporated by reference.

While often described herein as using an electrical stimulator to stimulate the patient's cochlear tissue via a cochlear electrode, in some examples, the system can additionally or alternatively include an acoustic stimulator 150. An acoustic stimulator can include, for example, a transducer (e.g., a piezoelectric transducer) configured to provide mechanical stimulation to the patient's ear structure. In an exemplary embodiment, the acoustic stimulator 150 can be configured to stimulate one or more portions of the patient's ossicular chain via amplified vibrations. Acoustic stimulators can include any appropriate acoustic stimulators, such as those found in the ESTEEM™ implant (Envoy Medical Corp., St. Paul, Minn.) or as described in U.S. Pat. Nos. 4,729,366, 4,850,962, and 7,524,278, and U.S. Patent Publication No. 20100042183, each of which is incorporated herein by reference in its entirety.

Figure 4:
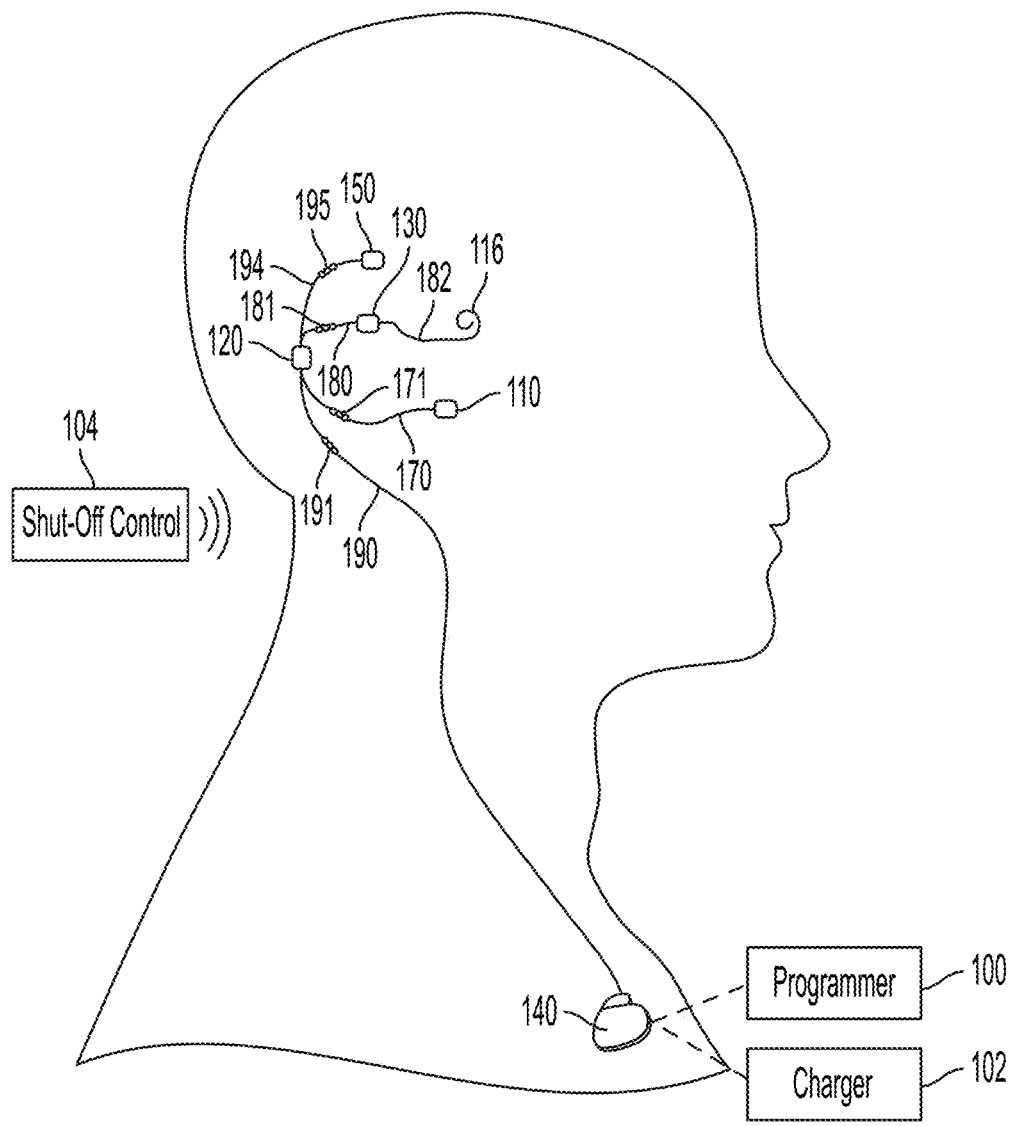
FIG. 4 is a schematic diagram illustrating an exemplary implantable system including an acoustic stimulator.

FIG. 4 is a schematic diagram illustrating an exemplary implantable system including an acoustic stimulator. The acoustic stimulator 150 can be implanted proximate the patient's ossicular chain and can be in communication with a signal processor via lead 194 and detachable connector 195. The signal processor can behave as described elsewhere herein and can be configured to cause acoustic stimulation of the ossicular chain via the acoustic stimulator 150 in in response to input signals from the inner ear sensor according to a transfer function of the signal processor.

The acoustic stimulator of FIG. 4 can be used similarly to the electrical stimulator as described elsewhere herein. For instance, an acoustic stimulator 150 can be mechanically coupled to a patient's ossicular chain upon implanting the system and coupled to the signal processor via lead 194 and detachable connector 195. Similarly to systems described elsewhere herein with respect to the electrical stimulator, if the signal processor requires replacement or repair, the signal processor can be disconnected from the acoustic stimulator (via detachable connector 195) so that the signal processor can be removed without disturbing the acoustic stimulator 150.

In general, systems incorporating an acoustic sensor such as shown in FIG. 4 can operate in the same way as systems described elsewhere herein employing an electrical stimulator and cochlear electrode only substituting electrical stimulation for acoustic stimulation. The same modularity benefits, including system maintenance and upgrades as well as the ability to convert to a fully implantable system when a patient becomes sufficiently developed, can be similarly realized using acoustic stimulation systems. For example, an acoustic stimulation system simply by substituting the electrical stimulator and cochlear electrode for an acoustic stimulator.

Some systems can include a hybrid system comprising both an electrical stimulator and an acoustic stimulator in communication with the signal processor. In some such examples, the signal processor can be configured to stimulate electrically and/or acoustically according to the transfer function of the signal processor. In some examples, the type of stimulation used can depend on the input signal received by the signal processor. For instance, in an exemplary embodiment, the frequency content of the input signal to the signal processor can dictate the type of stimulation. In some cases, frequencies below a threshold frequency could be represented using one of electrical and acoustic stimulation while frequencies above the threshold frequency could be represented using the other of electrical and acoustic stimulation. Such a threshold frequency could be adjustable based on the hearing profile of the patient. Using a limited range of frequencies can reduce the number of frequency domains, and thus the number of contact electrodes, on the cochlear electrode. In other examples, rather than a single threshold frequency defining which frequencies are stimulated electrically and acoustically, various frequencies can be stimulated both electrically and acoustically. In some such examples, the relative amount of electrical and acoustic stimulation can be frequency-dependent. As described elsewhere herein, the signal processor transfer function can be updated to meet the needs of the patient, including the electrical and acoustic stimulation profiles.

With further reference to FIGS. 1 and 4, in some examples, a system can include a shut-off controller 104, which can be configured to wirelessly stop an electrical stimulator 130 from stimulating the patient's cochlear tissue and/or an acoustic stimulator 150 from stimulating the patient's ossicular chain. For example, if the system is malfunctioning or an uncomfortably loud input sound causes an undesirable level of stimulation, the user may use the shut-off controller 104 to cease stimulation from the stimulator 130. The shut-off controller 104 can be embodied in a variety of ways. For example, in some embodiments, the shut-off controller 104 can be integrated into other external components, such as the programmer 100. In some such examples, the programmer 100 includes a user interface by which a user can select an emergency shut-off feature to cease stimulation. Additionally or alternatively, the shut-off controller 104 can be embodied as a separate component. This can be useful in situations in which the patient may not have immediate access to the programmer 100. For example, the shut-off controller 104 can be implemented as a wearable component that the patient can wear at all or most times, such as a ring, bracelet, necklace, or the like.

The shut-off controller 104 can communicate with the system in order to stop stimulation in a variety of ways. In some examples, the shut-off controller 104 comprises a magnet that is detectable by a sensor (e.g., a Hall-Effect sensor) implanted in the patient, such as in the processor and/or the implantable battery and/or communication module 140. In some such embodiments, when the magnet is brought sufficiently close to the sensor, the system can stop stimulation of the cochlear tissue or ossicular chain.

After the shut-off controller 104 is used to disable stimulation, stimulation can be re-enabled in one or more of a variety of ways. For example, in some embodiments, stimulation is re-enabled after a predetermined amount of time after it had been disabled. In other examples, the shut-off controller 104 can be used to re-enable stimulation. In some such examples, the patient brings the shut-off controller 104 within a first distance of a sensor (e.g., a magnetic sensor) to disable stimulation, and then removes the shut-off controller 104. Subsequently, once the patient brings the shut-off controller 104 within a second distance of the sensor, stimulation can be re-enabled. In various embodiments, the first distance can be less than the second distance, equal to the second distance, or greater than the second distance. In still further embodiments, another device such as a separate turn-on controller (not shown) or the programmer 100 can be used to re-enable stimulation. Any combination of such re-enabling of stimulation can be used, such as alternatively using either the programmer 100 or the shut-off controller 104 to enable stimulation or combining a minimum "off" time before any other methods can be used to re-enable stimulation.

In some embodiments, rather than entirely disable stimulation, other actions can be taken, such as reducing the magnitude of stimulation. For example, in some embodiments, the shut-off sensor can be used to reduce the signal output by a predetermined amount (e.g., absolute amount, percentage, etc.). In other examples, the shut-off sensor can affect the transfer function of the signal processor to reduce the magnitude of stimulation in a customized way, such as according to frequency or other parameter of an input signal (e.g., from the inner ear sensor).

With reference back to FIG. 1, as described elsewhere herein, the implantable battery and/or communication module can be used to provide power and/or data (e.g., processing instructions) to other system components via lead 190.

Different challenges exist for communicating electrical signals through a patient's body. For example, safety standards can limit the amount of current that can safely flow through a patient's body (particularly DC current). Additionally, the patient's body can act as an undesired signal path from component to component (e.g., via contact with the housing or "can" of each component). Various systems and methods can be employed to improve the communication ability between system components, such as those described in PCT Patent Application No. PCT/US20/19166, which is incorporated by reference.

Data can be communicated from the implantable battery and/or communication module to the signal processor for a variety of reasons. In some examples, data is that communicated to the implantable battery and/or communication module from an external component, such as a programmer as shown in FIG. 1. In an exemplary process, a programmer, such as a clinician's computer, can be used to communicate with a patient's fully implanted system via a communication configuration. For example, a programmer can communicate wirelessly (e.g., via Bluetooth or other appropriate communication technique) with the patient's implantable battery and/or communication module.

During such processes, a clinician can communicate with the signal processor, and, in some cases, with other components via the signal processor. For example, the clinician can cause the signal processor to actuate an electrical and/or an acoustic stimulator in various ways, such as using various electrical stimulation parameters, combinations of active contact electrodes, various acoustic stimulation parameters, and various combinations thereof. Varying the stimulation parameters in real time can allow the clinician and patient to determine effectiveness of different stimulation techniques for the individual patient. Similarly, the clinician can communicate with the signal processor to update transfer function. For example, the clinician can repeatedly update the transfer function signal processor while testing the efficacy of each one on the individual patient. In some examples, combinations of stimulation parameters and signal processor transfer functions can be tested for customized system behavior for the individual patient.

In some embodiments, various internal properties of the system may be tested. For instance, various impedance values, such as a sensor impedance or a stimulator impedance can be tested such as described in U.S. Patent Publication No. 2015/0256945 and in PCT Patent Application No. PCT/US20/19166, which are incorporated by reference.

While shown separately in FIGS. 1 and 4 for ease of reference and visualization, in some embodiments, an inner ear sensor (e.g., 110) can be integrated into a cochlear electrode (e.g., 116). For instance, in some examples, cochlear electrode 116 includes an included pressure transducer in communication with the signal processor 120. The processor can be configured to receive signals from the transducer as input signals from an inner ear sensor 110.

Figure 5:
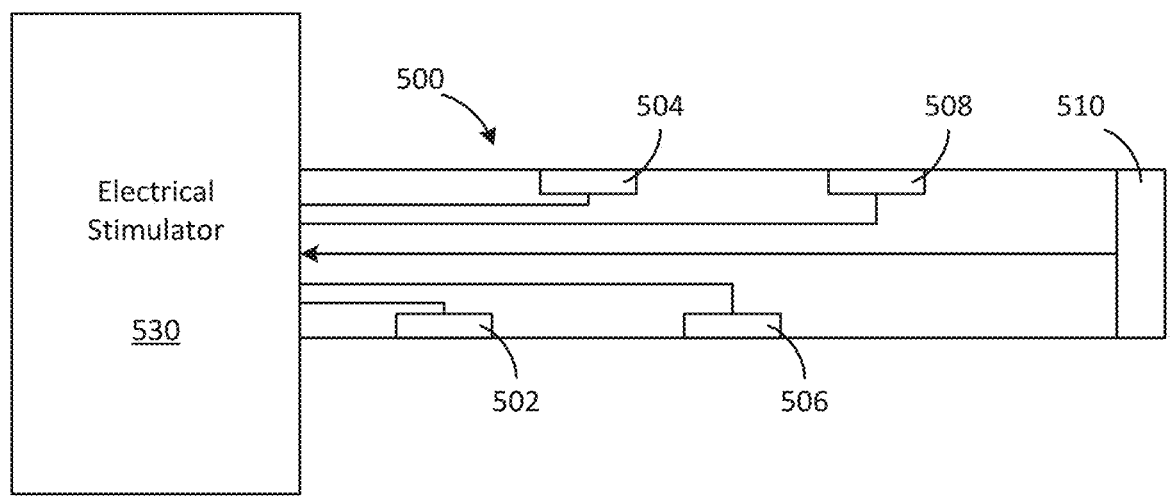
FIG. 5 is an example diagram showing an inner ear sensor as part of a cochlear electrode.

FIG. 5 shows an example cochlear electrode including an integral inner ear sensor. As shown, cochlear electrode 500 extends from an electrical stimulator 530, for example, into a wearer's cochlear tissue and/or fluid. The cochlear electrode 500 includes a plurality of contact electrodes (502, 504, 506, 508) configured to contact various portions of the cochlear tissue and/or fluid such as described elsewhere herein. While shown in the example of FIG. 5 as including four visible contact electrodes, in various embodiments, a cochlear electrode (e.g., 500) can include any number of contact electrodes.

The cochlear electrode of FIG. 5 further includes an inner ear sensor 510 configured to sense a pressure present in the cochlear tissue. The inner ear sensor 510 included in the cochlear electrode 500 can be configured to output an electrical signal to the signal processor based on a detected pressure in the cochlear tissue. While shown as being positioned at the distal end of the cochlear electrode 500, in various embodiments, inner ear sensor 510 can be positioned anywhere along the cochlear electrode 500. In some examples, the inner ear sensor 510 can be embodied as a ring sensor surrounding the cochlear electrode or as any other shape or type of sensor supported by the cochlear electrode. Moreover, in some examples, while only a single sensor 510 is shown in the example of FIG. 5, in various embodiments, a cochlear electrode can include any number of sensing components to perform the operation of the inner ear sensor. For instance, in some examples, the inner ear sensor comprises one or more pressure sensors supported by the cochlear electrode.

Including the inner ear sensor as a part of the cochlear electrode, such as is shown in the example of FIG. 5, reduces the number of components that must be implanted by a surgeon when implanting the system. For example, when the inner ear sensor is included with the cochlear electrode, the surgeon only needs to implant the cochlear electrode in order to also implant the input source when the inner ear sensor is used as the input source. This can simplify the implant surgery and make performing the surgery more consistent with traditional cochlear implant surgical procedures.

Additionally, in some cases, infants and children may not be suited for certain fully implantable systems including certain types of sensors, since changing anatomy as the wearer grows may impact the efficacy of certain components implanted when the wearer was younger. However, an inner ear sensor, such as one integrated into a cochlear electrode such as shown in FIG. 5, may be implanted and used as an input source to a cochlear implant system independent of the physical development of the wearer. Accordingly, systems including an inner ear sensor as an input source may be fully implanted into a wearer without need for future surgeries or other changes to accommodate different sensors once the wearer has fully developed.

While shown in several embodiments (e.g., FIGS. 1 and 4) as being separate components connected by a lead (e.g., lead 180), in some examples, the processor (e.g., 120) and the stimulator (e.g., 130) can be integrated into a single component, for example, within a hermetically sealed housing. Examples of such implementations are described in PCT Patent Application No. PCT/US20/19166, which is incorporated by reference.

Figure 6A:
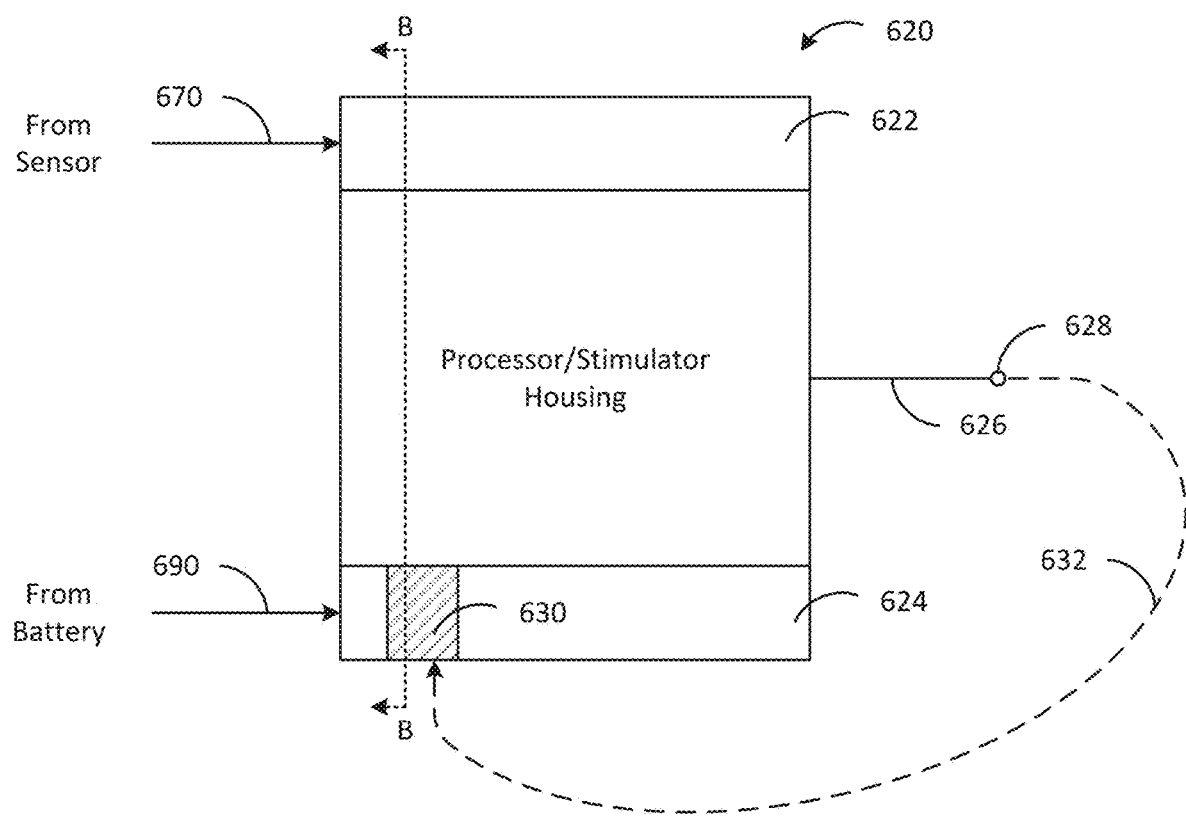
FIG. 6A shows an exemplary schematic illustration of processor and stimulator combined into a single housing.

FIG. 6A shows an exemplary schematic illustration of processor and stimulator combined into a single housing. In the example of FIG. 6A, the processor/stimulator 620 receives signal inputs from the sensor (e.g., an inner ear sensor) via lead 670 and power from a battery (e.g., the implantable battery and/or communication module) via lead 690. The processor/stimulator 620 can include headers 622, 624 for receiving leads 670, 690, respectively.

The processor/stimulator 620 can be configured to receive an input signal from the sensor, process the received input signal according to a transfer function, and output a stimulation signal via electrode 626. Electrode 626 can include one or more contact electrodes (e.g., 628) in contact with a wearer's cochlear tissue to provide electrical stimulation thereto, for example, as described PCT Patent Application No. PCT/US20/19166, which is incorporated by reference.

The processor/stimulator 620 of FIG. 6A includes a return electrode 630 for providing a return path (e.g., 632) for stimulation signals emitted from electrode 626. The return electrode 630 can be electrically coupled to a ground portion of circuitry within the processor/stimulator 620 to complete a circuit comprising circuitry within the processor/stimulator 620, the electrode 626, the wearer's cochlear tissue, and ground. In some examples, the return electrode 630 comprises an electrically conductive material in electrical communication with circuitry inside the processor/stimulator 620, while the rest of the housing of the processor/stimulator 620 is generally not electrically coupled to internal circuitry.

In some embodiments, the return electrode 630 and the housing of the processor/stimulator 620 comprise electrically conductive materials. For instance, in some examples, the housing comprises titanium while the return electrode 630 comprises platinum or a platinum alloy. Header 624 can generally include a non-conductive biocompatible material, such as a biocompatible polymer. The non-conductive header 624 can provide isolation between the return electrode 630 and the conductive housing of the processor/stimulator 620.

While shown in FIG. 6A as being positioned in the power header 624 of the processor/stimulator 620, in general, the return electrode 630 can be positioned anywhere on the exterior surface of the processor/stimulator 620. In some examples, one or more redundant return electrodes can be included, for example, at or near the interface of the housing and the electrode 626. In some examples, a return electrode can be positioned on a proximal end of the electrode 626 itself. In some embodiments having a plurality of return electrodes (e.g., return electrode 630 and a return electrode on the proximal end of electrode 626), a switch can be used to select which return electrode is used. Additionally or alternatively, a plurality of return electrodes can be used simultaneously.

Figure 6B:
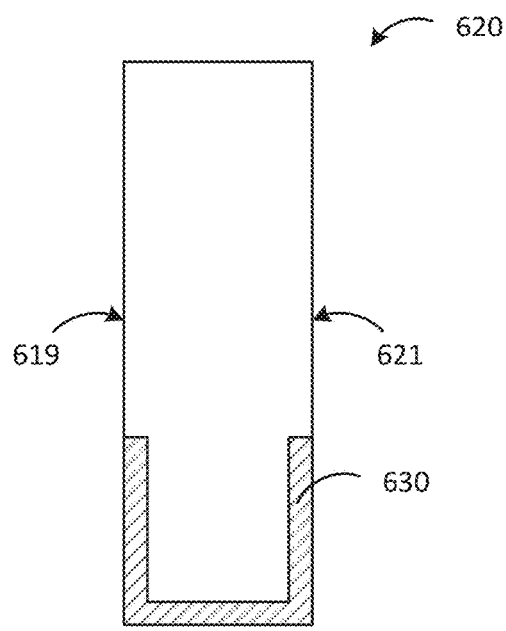
FIG. 6B shows a simplified cross-sectional view of the processor/stimulator shown in FIG. 6A taken along lines B-B.

FIG. 6B shows a simplified cross-sectional view of the processor/stimulator shown in FIG. 6A taken along lines B-B. As shown in FIG. 6B, processor/stimulator 620 includes a housing having a first side 619 and a second side 621 and a return electrode 630 embedded in the housing. Return electrode 630 can comprise a conductive material suitable for contact with a wearer's tissue, such as platinum. In the illustrated example, the return electrode 630 wraps around to both sides of the housing of the processor/stimulator 620 so that the return electrode 630 is coupled to the outer surface of the housing on the first side 619 and the second side 621.

This can facilitate implanting onto either side of a wearer's anatomy, since in some cases, only one side of the processor/stimulator electrically contacts conductive tissue of the wearer while the other side contacts, for instance, the skull of the wearer, and does not easily provide the return path (e.g., 632). Thus, a single processor/stimulator design can be implanted in either side of a wearer's anatomy while providing an adequate return path via a return electrode 630.

In various examples, the return electrode 630 can extend around a perimeter edge of the processor/stimulator 620, as shown in FIG. 6B. In other examples, the return electrode 630 can include sections on either side of the housing and can be connected to one another internally within the housing rather than via a wrap-around contact. Additionally, while shown as being embedded in the housing of the processor/stimulator 620, in some examples, return electrode 630 can protrude outwardly from the housing. Return electrode 630 can generally be any of a variety of shapes and sizes while including an electrical contact section on opposing sides of the housing to provide usability on either side of a wearer's anatomy. In other embodiments, return electrode can be positioned only one side of the housing for a customized right-side or left-side implementation.

As described elsewhere herein, in various embodiments, the processor generally receives an input signal, processes the signal, and generates a stimulation signal, which can be applied via an integrated stimulator (e.g., via a processor/stimulator such as in FIGS. 6A and 6B) or a separate stimulator in communication with the processor (e.g., as shown in FIGS. 1 and 4). In some such embodiments, the input signal received via the signal processor is generated by an implantable sensor, such as an inner ear sensor.

However, such sensors often measure or otherwise receive some stimulus that is converted into an output that is read and processed by the signal processor. For example, some inner ear sensors may produce a different output signal for a given stimulus depending on a variety of factors, such as variability in a wearer's inner-ear anatomy and motion. Thus, the output of a sensor for a given input may be not predictable while designing a system, especially across a range of frequencies.

Figure 7B:
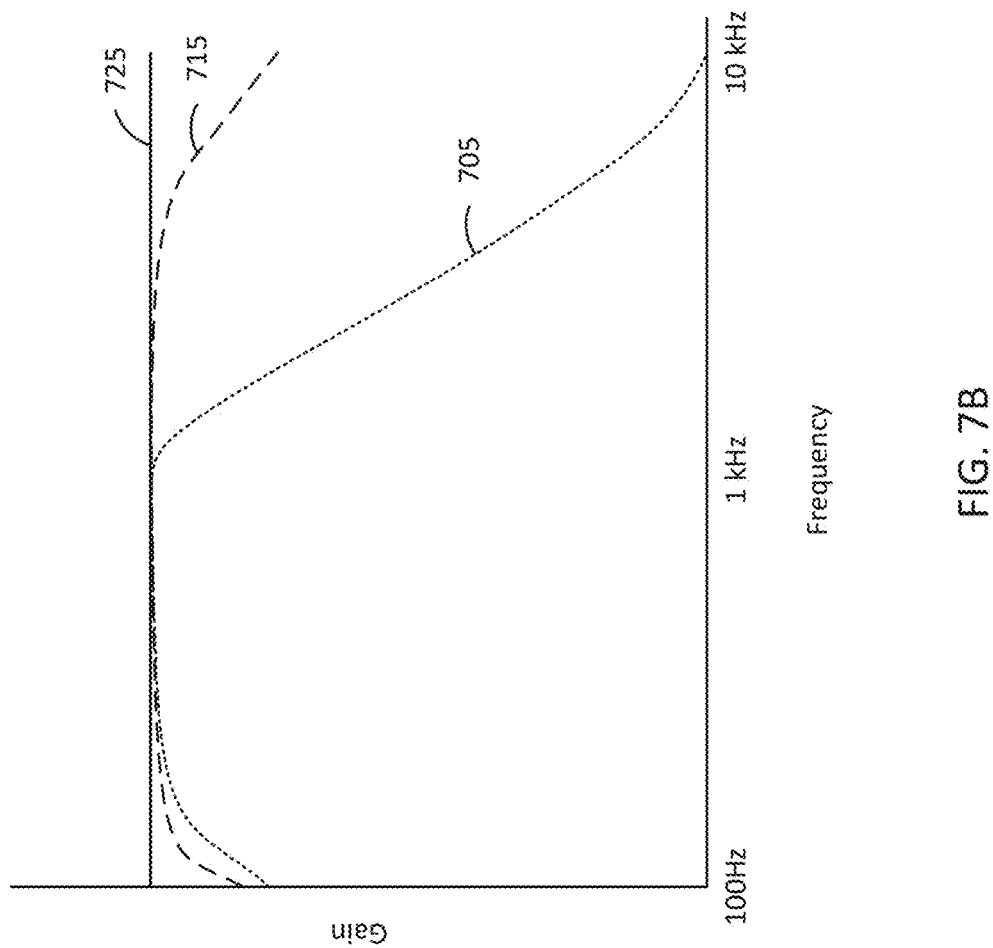
FIG. 7B shows an exemplary gain vs. frequency response curve for signals at various stages in the processing configuration.
Figure 7A:
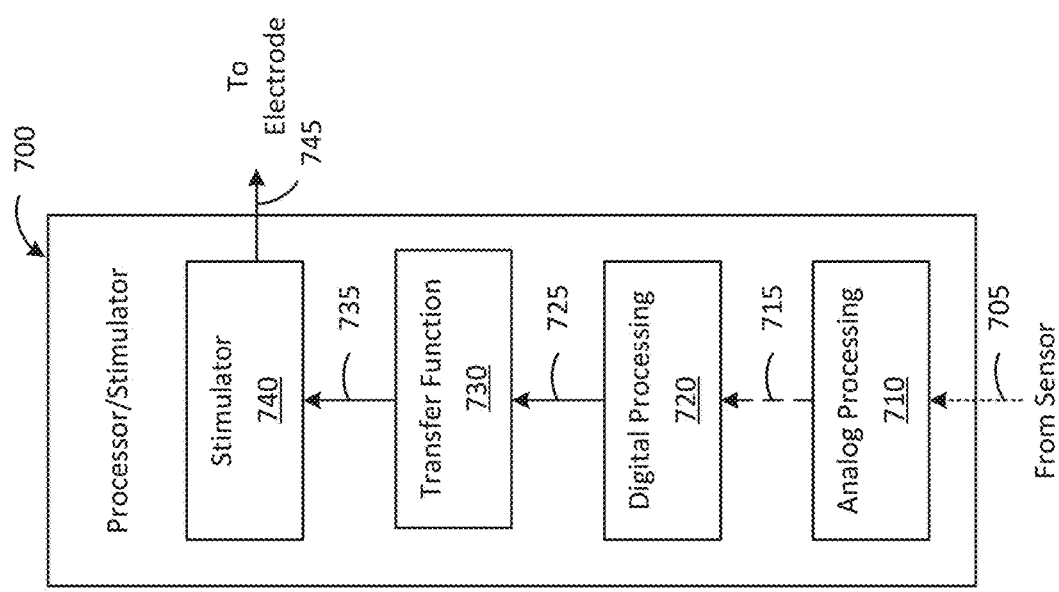
FIG. 7A is a schematic diagram showing an exemplary signal processing configuration for adapting to variability in a sensor frequency response.

FIG. 7A is a schematic diagram showing an exemplary signal processing configuration for normalizing a stimulus signal and adapting to variability in a sensor frequency response. FIG. 7B shows an exemplary gain vs. frequency response curve for signals at various stages in the processing configuration. "Gain" associated with a particular frequency, as used with respect to FIG. 7B, refers to a relationship (e.g., a ratio) between the magnitude of an input stimulus received by the sensor (e.g., an inner ear sensor) and processor and the magnitude of the resulting signal at various stages of processing. In the illustrated example, the processor/stimulator 700 receives an input signal 705 from the sensor (e.g., the inner ear sensor).

As shown in FIG. 7B, the gain is very uneven over the distribution of frequencies shown in the plot. For instance, according to the illustrated example, a stimulus signal received at the sensor at 1 kHz will result in a much larger magnitude in signal 705 compared to a stimulus signal of the same magnitude received at the sensor at 10 kHz. Such a discrepancy in frequency response can make signal processing difficult. Moreover, such frequency response in general may vary from person to person, or over the course of a wearer's lifetime due to physical movement of a sensor (e.g., an inner ear sensor) or anatomical changes of the wearer.

The input signal 705 undergoes analog processing 710 to produce an analog processed signal 715. As shown in FIG. 7B, the analog processing step 710 improves the consistency of the gain across the range of frequencies, as the analog processed signal 715 provides a flatter frequency response curve than does the input signal 705. In some embodiments, the analog processing can include one or more filter and/or amplifiers generally configured to flatten out the frequency response curve as shown in FIG. 7B. In some examples, the analog processing components 710 within the processor/stimulator 700 can be substantially the same across various implantable systems in order to provide a first order correction of the frequency response. In other examples, an analog processing configuration 710 can be customized to the wearer, for example, based on known anatomical features, measurements, analysis, or the like.

The analog processed signal 715 undergoes a digital processing step 720 to produce a digitally processed signal 725. As shown in FIG. 7B, the digital processing step 720 further improves the consistency of the gain across the range of frequencies, as the digitally processed signal 725 provides a flatter frequency response curve than does the analog processed signal 715. In some embodiments, the digital processing 720 can be configured to substantially flatten the frequency response to correct remaining frequency response inconsistencies in the analog processed signal 715. For instance, in some embodiments, after digital processing 720, a stimulus signal of a given magnitude at a first frequency and a second frequency will result in a digitally processed signal 725 having the same magnitude at the first and the second frequencies. Thus, the digitally processed signal 725 corresponds to a normalized stimulus signal, reducing or eliminating the variability that comes with different wearer anatomies and wearer motion and/or changes over time. Having a normalized frequency response across large frequency ranges can simplify assessment of the efficacy of the implanted system, programming a signal processor transfer function, assessing system operation, and the like. In some examples, a flat frequency response can enable the system to present an electrical stimulus to the wearer at appropriate intensity levels, for example, with respect to received external acoustic stimuli, independent of the frequency content of the external acoustic stimuli.

In some embodiments, the digital processing 720 can be customized via a calibration process after the system has been implanted. In an exemplary calibration process, a clinician or other user may provide a series of stimulus signals, for instance, at a plurality of frequencies and having like amplitudes, to be "picked up" by the sensor, which generates an input signal 705 for each received signal. The clinician or other user may then sample the resulting analog processed signal 715 and/or an initial digitally processed signal 725 at the plurality of frequencies to determine the remaining non-uniformity in gain across the frequency sweep. The digital processing 720 can be either established or updated to compensate for non-uniformities in order to establish a substantially flat frequency response curve in the digitally processed signal 725. In some examples, a plurality of signals having different frequencies are provided in sequence and a magnitude response (e.g., gain) at each frequency is determined. After determining such a magnitude response, the digital processing stage 720 can be updated based on the response vs. frequency relationship in order to flatten the frequency response curve.

In an alternate process, a white noise signal can be provided to be "picked up" by the sensor. A transform (e.g., a Fast Fourier Transform, or FFT) of the signal can be performed in order to extract the frequency content of the signal. The extracted frequency content can used to determine a magnitude response at each frequency and the digital processing 720 can be updated to flatten the frequency response similar to described above.

In the illustrated example of FIG. 7A, the digitally processed signal 725 (e.g., having a uniform gain across a frequency range with respect to input signals received from the sensor) is processed according to the signal processor transfer function 730 to generate a stimulation signal 735. Stimulation signal 735 can be received by the stimulator 740, which can apply an electrical signal 745 to the electrode such as described elsewhere herein.

In some examples, the digital processing step 720 to provide a uniform frequency response can be incorporated into the transfer function 730 wherein the analog processed signal 715 is digitally processed to both flatten the frequency response and to generate a stimulation signal (e.g., 735) according to a programmed transfer function. Additionally or alternatively, as described elsewhere herein, in some examples, stimulator 740 can be located external to the processor rather than being combined as a single processor/stimulator component 700.

As described elsewhere herein, while many examples described herein use an inner ear sensor being in communication with an implanted signal processor, in various embodiments, one or more additional or alternative input sources can be included. For instance, in some embodiments, a microphone can be implanted under a user's skin and can be placed in communication with the signal processor (e.g., via a detachable connector such as 171). The signal processor can receive input signals from the implanted microphone and provide signals to the stimulator based on the received input signal and the signal processor transfer function.

Figure 8:
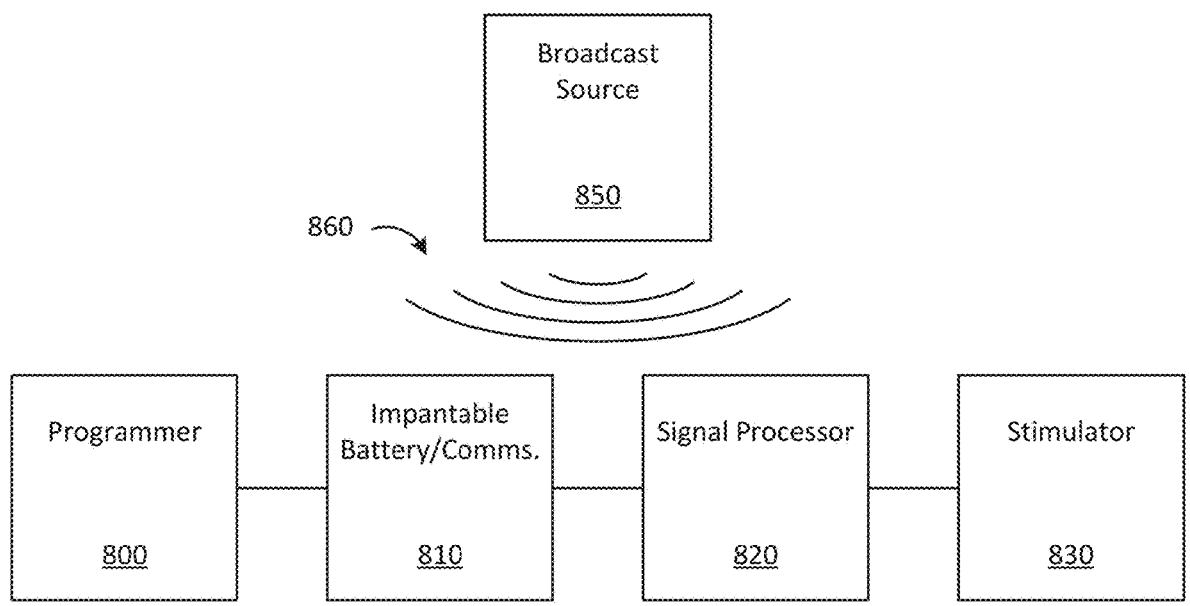
FIG. 8 is a schematic system diagram showing an implantable system configured to receive broadcast signals from a broadcast device.

Additionally or alternatively, one or more system components can be configured to receive broadcast signals for converting into stimulation signals. FIG. 8 is a schematic system diagram showing an implantable system configured to receive broadcast signals from a broadcast device. As shown in the example of FIG. 8, a broadcast source 850 broadcasts a signal via communication link 860. The communication link 860 can include communication via a variety of communication protocols, such as Wi-Fi, Bluetooth, or other known data transmission protocols. Broadcast source 850 can include any of a variety of components, such as a media source (e.g., television, radio, etc.), communication device (e.g., telephone, smartphone, etc.), a telecoil or other broadcast system (e.g., at a live performance), or any other source of audio signals that can be transmitted to an implanted system or to an external component of an implanted system (e.g., a system programmer, etc.).

An implantable system including a programmer 800, an implantable battery and/or communication module 810, a signal processor 820, and a stimulator 830 can generally receive the data from the broadcast source 850 via communication link 860. In various embodiments, any number of components in the implantable system can include a receiving device, such as a telecoil, configured to receive broadcast signals for eventual conversion into stimulation signals.

For instance, in some embodiments, programmer 800 can include a telecoil relay configured to receive broadcast telecoil signals from a broadcast source 850. The programmer can be configured to subsequently communicate a signal representative of the received broadcast signal to the implantable battery and/or communication module 810 and/or the signal processor 820, e.g., via a Bluetooth communication. If the communication is received from the programmer 800 via the implantable battery and/or communication module 810, the implantable battery and/or communication module 810 can communicate the signal to the signal processor, for example, as described in PCT Patent Application No. PCT/US20/19166, which is incorporated by reference.

In some such embodiments, the signal processor 820 can be configured to receive such signals from the implantable battery and/or communication module 810 and output stimulation signals to the stimulator 830 based on the received signals and the signal processor transfer function. In other examples, the signal processor 820 can include a telecoil relay or other device capable of receiving broadcast signals from the broadcast source 850. In some such embodiments, the signal processor 820 processes the received signals according to the signal processor transfer function and outputs stimulations signals to the stimulator 830.

In some embodiments, the signal processor 820 can be in communication with a plurality of input sources, such as, for example, a combination of an implanted microphone, an inner ear sensor, and a broadcast source 850 (e.g., via the implantable battery and/or communication module 810). In some such examples, the signal processor can be programmed with a plurality of transfer functions, each according to respective input sources. In such embodiments, the signal processor can identify which one or more input sources are providing input signals and process each such input signal according to the transfer function associated with its corresponding input source.

In some examples, a signal processor 820 receiving a plurality of input signals from a corresponding plurality of input sources effectively combines the signals when producing a stimulation signal to the stimulator 830. That is, in some embodiments, input sources are combined to form the stimulation signal from the signal processor 820. In some such examples, a user may be able to mix the various received input signals in any way desired. For example, a user may choose to blend a variety of different input streams, such as an input from an inner ear sensor or other implanted device, a signal received from an external device (e.g., a telecoil relay, a Bluetooth connection such as to a smartphone, etc.), and the like. In an exemplary configuration, a user may elect to equally blend two input sources such that the stimulation signal is based 50% on a first input source and 50% on a second input source.

Additionally or alternatively, a user may elect to effectively "mute" one or more input sources so that the signal processor 820 outputs stimulations signals based on input signals received from unmuted sources. Similarly, a user may be able to select a single source from which to process received input signals. For example, in some embodiments, a user may select to have signals received from broadcast source 850 processed and converted into stimulation signals while having signals received from, for example, an inner ear sensor, disregarded.

In some examples, direct communication with the signal processor can be used to test the efficacy of a given signal processor transfer function and associated stimulation (e.g., acoustic or electrical) parameters. For example, the programmer can be used to disable input signals from an inner ear sensor or other input source and provide a customized signal to the signal processor to simulate a signal from the input source. The signal processor processes the received signal according to its transfer function and actuates the electrical stimulator and/or the acoustic stimulator accordingly. The processor can be used to test a variety of customized "sounds" to determine the efficacy of the signal processor transfer function for the given patient for each "sound."

Various features and functions of implantable systems have been described herein. As described, in various embodiments, system operation(s) can be adjusted based on communication with the implanted system from components located outside of the body while the system remains implanted, such as an external device. External devices may include a variety of systems, such as a programmer, a charger, a smartphone, a tablet, a smartwatch or other wearable technology and a fob. In some examples, such components can communicate with one or more implantable components via one or more communication protocols via wireless communication link, such as Bluetooth, Zigbee, or other appropriate protocols. In various embodiments, different external devices are capable of performing one or more functions associated with system operation. In some such embodiments, each external device is capable of performing the same functions as the others. In other examples, some external devices are capable of performing more functions than others, such as described in PCT Patent Application No. PCT/US20/19166, which is incorporated by reference.

As described, in some embodiments, various devices can communicate with components in an implanted system via wireless communication protocols such as Bluetooth. Various data and signals can be communicated wirelessly, including control signals and streaming audio. However, in some cases, such wireless communication should be made secure so that a system only communicates with those devices desired by the wearer. This can prevent unwanted signals from being broadcast to an implanted device and/or unauthorized access to one or more adjustable device settings.

In some embodiments, one or more implanted system components comprises a near field communication component configured to facilitate communication between the system and an external device only when brought into very close proximity to the near field communication component. In some such examples, once near-field communication is established, the pairing for longer-range wireless communication (e.g., Bluetooth) can be established. For instance, in an exemplary embodiment, a charger and an implantable battery and/or communication module can each include near field communication components for establishing a secure, near field communication and subsequently pairing to each other for additional wireless communication. Exemplary systems and methods for establishing a secure wireless connection are described in PCT Patent Application No. PCT/US20/19166, which is incorporated by reference.

In some embodiments, once an external device is paired with the implantable battery and/or communication module 140, the external device may be used to perform additional functions. In some embodiments, the additional functions may comprise adjusting a transfer function of the signal processor. In some examples, the external device includes or otherwise communicate with one or more sensors and can be configured to update the transfer function of the signal processor based on one or more signals detected via the one or more sensors. In some such examples, one or more such sensors can include a microphone, a location sensor (e.g. GPS, location based on one or more available wireless networks, etc.), a clock, or other sensors known to one of ordinary skill in the art. In some embodiments, external device including or in communication with such one or more sensors includes a smartphone, tablet, or computer. Exemplary systems and methods for establishing a secure wireless connection are described in PCT Patent Application No. PCT/US20/19166, which is incorporated by reference.

As described, in various embodiments, different external devices can interface with implanted components to adjust operation of the system in various ways. In some embodiments, not all components are capable of performing the same functions as other components. Generally, the modularity of such systems allows system modifications, such as repairing, replacing, upgrading, etc., of system components and/or transitioning from a partially- to fully-implantable system, to be performed with minimal disturbance of implanted system components. For example, an implanted cochlear electrode and electrical stimulator and/or acoustic stimulator can remain in place while other system components are implanted and/or replaced, reducing the risk of additional procedures damaging the patient's cochlear tissue. Additionally, the communication techniques as described herein can be used to help customize and/or optimize a signal processor transfer function for a particular patient, as well as enable the system to meet safety standards, provide adequate power and data transfer rates between system components, and operate at a high efficiency. It will be appreciated that, while generally described herein with respect to implantable hearing systems, communication techniques described can be used in a variety of other implantable systems, such as various neuromodulation devices/systems, including, for example, pain management, spinal cord stimulation, brain stimulation (e.g., deep brain stimulation), and the like.

Figure 9:
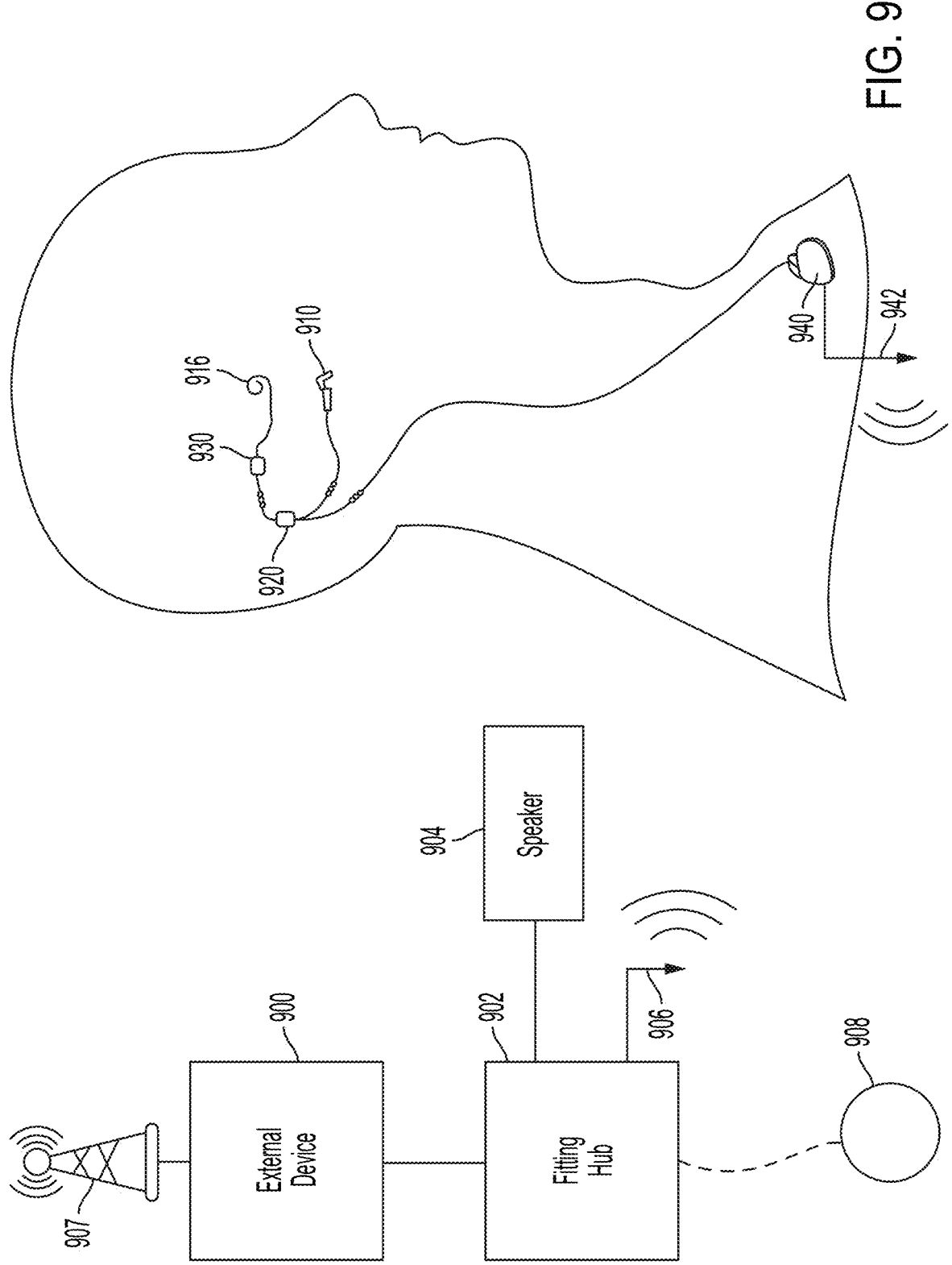
FIG. 9 shows an example configuration of an interfacing device configured to assist in system calibration.

In some embodiments, systems can communicate with external devices to assist in fitting and/or calibrating the implanted system. FIG. 9 shows an example configuration of an interfacing device configured to assist in system calibration. As shown, an external device 900 (e.g., a laptop, PC, smartphone, tablet, smartwatch, etc.) communicates with a fitting hub 902. The fitting hub 902 includes or otherwise communicates with a speaker 904, which can output a sound based on a command from the fitting hub 902.

In the illustrated example, fitting hub 902 includes a wireless communication interface 906 (e.g., a Bluetooth interface) that can communicate with a communication interface 942 of an implantable battery and/or communication module 940. In some examples, the fitting hub 902 includes or is otherwise capable of interfacing with a near field communication component 908 (e.g., a communication coil) to enable Bluetooth communication between the fitting hub 902 and an implanted system (e.g., via an implantable battery and/or communication module 940) such as described elsewhere herein. Additionally or alternatively, another device (e.g., a charger) can be used to enable wireless (e.g., Bluetooth) communication between the fitting hub 902 and the implantable battery and/or communication module 940.

The illustrated system of FIG. 9 includes an implanted modular cochlear implant system including an implantable battery and/or communication module 940, a signal processor 920, a sensor 910 (e.g., an inner ear sensor), a stimulator 930, and a cochlear electrode 916. Such components can be configured and arranged similar to various embodiments described herein and can configured to provide electrical signals from the stimulator 930 via the cochlear electrode 916 based on signals received at the signal processor from the sensor 910.

During an exemplary calibration process, the fitting hub 902 can be configured to output a sound via speaker 904 and also communicate information about the sound (e.g., intensity, frequency content, etc.) to the implantable battery and/or communication module 940 of the implanted system. The implanted system, e.g., via the signal processor 920, fitting hub 904, or implantable battery and/or communication module, can be configured to compare the output of the sensor 910 (received at the signal processor 920) to the actual sound emitted from the speaker 904. This data can be repeated for a plurality of sounds from output from the speaker (e.g., various frequencies and/or amplitudes) and used to determine the relationships between sounds picked up from the sensor 910 and the output from the sensor 910 to the signal processor 920. Based on this information, the signal processor 920 transfer function can be calibrated so that stimulation signals sent to the stimulator 930 based on the output from the sensor 910 accurately represent the sound from the environment. Additionally or alternatively, the information can be used to identify how effectively the sensor responds to various external acoustic stimuli, such as different frequencies, intensities, etc. This information can be determined specifically for the wearer, since the sensor response may depend on various factors specific to the wearer and/or the positioning of the sensor.

In some embodiments, the fitting hub 902 may be configured to output one or more sounds comprising a single frequency and/or single intensity. For example, each sound may have a signal frequency component at an intensity, such as various tones. Additionally or alternatively, the one or more sounds may comprise complex frequency and intensity components, such as sounds representing various beeps, words, noises, or other sounds known to one of ordinary skill in the art.

While described as taking place in the implanted system (e.g., the signal processor 920), the calibration process can be similarly performed via the fitting hub 902. For example, the speaker 904 can output a sound based on instructions from the fitting hub 902. The sensor 910 can output a signal based on the sensor response to the sound emitted from speaker 904, and the signal processor 920 can receive the signal from the sensor 910 and output stimulation signals to the stimulator 930 based on the receives signals and the signal processor transfer function.

In various examples, the implantable battery and/or communication module 940 can be configured to receive any combination of the signals from the sensor 910, the stimulation signals from the signal processor 920, or signals representative of one or both of such signals. The implantable battery and/or communication module 940 can then communicate one or more signals to the fitting hub 902 representative of the output of the sensor 910 and/or the signal processor 920 in response to the sound output from speaker 904. The comparison of the sound output from the speaker 904 and the corresponding resulting signal(s) in the implanted system can be performed via processing in the fitting hub 902. In some examples, the comparison can be performed in the implantable battery and/or communication module 940.

Similar to discussed above, such a comparison can be used to determine the relationships between sounds picked up from the sensor 910 and the output from the sensor 910 to the signal processor 920. Based on this information, the signal processor 920 transfer function can be calibrated so that stimulation signals sent to the stimulator 930 based on the output from the sensor 910 accurately represent the sound from the environment. Additionally or alternatively, the information can be used to identify how effectively the sensor responds to various external acoustic stimuli, such as different frequencies, intensities, etc. This information can be determined specifically for the wearer, since the sensor response may depend on various factors specific to the wearer and/or the positioning of the sensor.

As described, in various examples, the external device 900 can be used in conjunction with the fitting hub 902. For instance, in some examples, the external device 900 can provide processing and control capabilities for processes described herein, and the fitting hub 902 can act as the interface between the external device 900 and the implanted system (e.g., by providing speaker 904, wireless communication interface 906, near field communication component 908, etc.).

In some embodiments, features and/or functions of the fitting hub 902 as described herein can be performed via the external device, such as via a laptop, PC, smartphone, tablet, etc. including various capabilities described with respect to the fitting hub. For instance, an external device can include a speaker capable of outputting desired sounds according to a command from the external device, as well as a wireless communication interface for communicating with the implanted system, e.g., via implantable battery and/or communication module 940.

In some examples, the external device 900 and/or the fitting hub 902 may comprise a user interface in the form of an application on the external device. In such embodiments, features and/or functions of the fitting hub 902 can be performed via the application. For instance, in some examples, the fitting hub can receive instructions to perform functions via an application running on the external device 900. In some such embodiments, a wearer and/or physician can provide an input via the application, for example, during various processes described herein. In some embodiments, a wearer can receive a sound from the fitting hub 902 and provide input, via the application, indicating whether the sound was heard or not heard, was too loud or too quiet, was distinguishable or not distinguishable from a previous sound, and/or other inputs. In some examples, an implant system (e.g., via fitting hub 902 or implantable battery and/or communication module 940) can be configured to update a signal processor transfer function in response to such received inputs.

In some embodiments, the fitting hub 902 and/or the external device 900 may be configured to communicate to a remote facility, for example, with a physician such as an audiologist. In some such embodiments, the fitting hub 902 and/or the external device 900 includes a remote communication device 907 configured to communicate with such a remote facility, for example, via the internet. The remote communication device 907 can communicate various information associated with the fitting hub 902, the external device 900, and the implanted cochlear implants, to an additional device, such as a device used by an audiologist. Additionally or alternatively, the remote communication device 907 can be configured to receive inputs from such an additional device, such as inputs related to features and/or functions performed by the fitting hub, the external device, and/or the implanted cochlear implants. For example, in some instances, an audiologist operating at a remote facility can trigger the fitting hub 902 to output one or more predetermined sounds and/or perform one or more fitting functions. Additionally or alternatively, the audiologist can receive information such as how often the wearer uses and/or updates features of the cochlear implant system.

In an example implementation, a physician can receive diagnostic information regarding any testing or other processes performed by the external device 900, the fitting hub 902, and/or the implanted cochlear implant system via the remote communication device 907. In some such examples, the physician may receive data regarding how often tests or other processes are performed, the results of any performed tests or processes, how often various devices (e.g. fitting hub 902) are used, and/or any feedback regarding the use or usability of the implanted cochlear implants.

In some examples, the physician can initiate or perform various tests or other processes from an additional device via the remote communication device 907. In some embodiments, features and/or functions of the fitting hub 902 as described herein can be performed or initiated by a physician using an additional device via the remote communication device 907. In various examples, the physician can perform various features, such as providing one or more sounds via a speaker (e.g., 904), performing a stapedial reflex test, or the like as described herein. The physician can receive one or more signals representative of the output of the sensor 910 (e.g., an inner ear sensor) and/or the signal processor 920 in response to the provided one or more sounds from the speaker. A comparison of the provided one or more sounds form the speaker and the corresponding resulting signal(s) in the implanted system can be performed by the additional device and/or by the physician receiving such information via the additional device.

In some embodiments, the remote communication device 907 may communicate with an additional device (e.g., at a physician's remote facility) via a wireless connection (e.g. Bluetooth, Wi-Fi, NFC, cellular network, internet access, etc.). While the remote communication device 907 is depicted as communicating via the external device 900, the remote communication device 907 can additionally or alternatively communicate via the fitting hub 902, or a different component of the system. In various embodiments, such a remote communication device can be integrated into the external device 900 and/or the fitting hub 902. In some embodiments, the remote communication device 907 and the wireless communication interface 906 may be integrated together to facilitate communication with a remote facility and an implanted system. Alternatively, the remote communication device 907 and the wireless communication interface 906 may be separate, or partially separate components.

Figure 10:
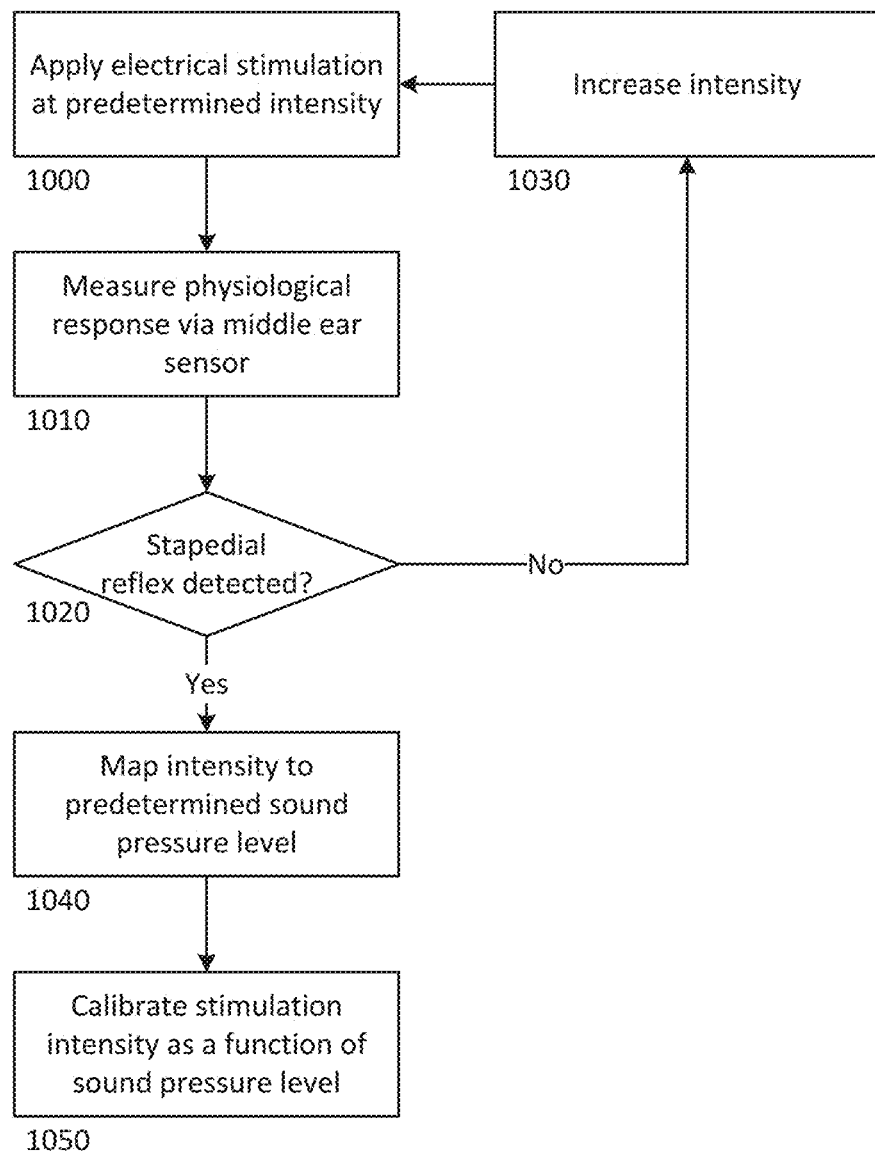
FIG. 10 is a process flow diagram showing an example process for calibrating an implanted system.

FIG. 10 is a process flow diagram showing an example process for calibrating an implanted system. In some examples, one or more sensors (e.g., an inner ear sensor 110) can detect a physiological phenomenon known as a stapedial reflex, in which muscles in the middle ear contract in response to various stimuli, such as loud sounds or the expectation of loud sounds. In some examples, an implanted signal processor in communication with such a sensor (e.g., an inner ear sensor) can recognize the occurrence of a stapedial reflex based on a characteristic output, for instance, via preprogrammed signal recognition or via a learning process, in which the stapedial reflex is triggered and the response from the sensor is measured and learned. In various examples, such stapedial reflex detection can be performed using signals received from a variety of sensors. In some examples, an output of an inner ear sensor can be monitored and a stapedial reflex detected based on a characteristic output or change in output of the inner ear sensor, such as a change in signal amplitude. Similarly, in some examples, a stapedial reflex can be detected based on a characteristic output or change in output of a middle ear sensor, such as described in PCT Patent Application No. PCT/US20/19166, which is incorporated by reference The calibration process of FIG. 10 includes applying electrical stimulation at a predetermined intensity (step 1000) and measuring a physiological response via an inner ear sensor (step 1010). The measured physiological response can be used to detect whether or not a stapedial reflex has occurred (step 1020). If a stapedial reflex is not detected, the intensity of the electrical stimulation is increased (step 1030), and electrical stimulation at the new intensity is applied (step 1000) and the physiological response is measured (step 1010). This process can be repeated until the stapedial reflex is detected at step 1020.

Once the stapedial reflex is detected, the intensity that caused the stapedial reflex can be mapped to a predetermined sound pressure level (step 1040). For instance, in some examples, the lowest electrical intensity determined to cause the detected stapedial reflex can be mapped to an input sound pressure of 100 dB. The method can include calibrating stimulation intensities as a function of sound pressure level (step 1050) based on the mapping of the stapedial reflex-causing intensity to the predetermined sound pressure level.

The calibration process of FIG. 10 can be initiated in a variety of ways. For example, in various embodiments, the process can be initiated by one or more components in communication with the implanted system, such as a programmer, charger, external device, fitting hub, or the like. Such processes can be performed during an initial fitting and/or a calibration after a period of use of the system.

Leveraging fully implanted system and initiating the process via a wireless communication (e.g., from a programmer, fitting hub, external device etc.), greatly simplifies the process of triggering and/or detecting the stapedial reflex. For example, utilizing a cochlear electrode (e.g., 916) to cause the stapedial reflex and sensing the reflex using an implanted inner ear sensor eliminates the need for tedious diagnostic equipment such as tympanometry equipment for analyzing a stapedial reflex.

In some examples, the systems and processes described with respect to FIG. 9 can be used in the calibration steps discussed with respect to FIG. 10. For instance, in an illustrative example, the fitting hub 902 of FIG. 9 can cause a speaker 904 to produce a sound having a sound pressure level of 100 dB while also communicating (e.g., via Bluetooth communication) the details of the sound (e.g., intensity, frequency, etc.) to the implantable battery and/or communication module 940. The output of the sensor 910 in response to the 100 dB sound can be identified and associated with the lowest electrical stimulation intensity that causes the detected stapedial reflex. Such a process can be repeated for a plurality of frequencies to link various external acoustic stimuli (e.g., from speaker 904) to particular electrical stimulations.

Several embodiments discussed herein generally relate to a cochlear implant system. As discussed herein, cochlear implant systems can comprise a cochlear electrode implanted into the cochlear tissues of a wearer, as well as various other components such as an electrical stimulator, signal processor, and an inner ear sensor. In some embodiments, the cochlear implant system comprises components implanted into one or both sides of a wearer. For example, a system can comprise components implanted in a wearer's left side (e.g. for their left ear), their right side (e.g. for their right ear), or both.

Figure 11:
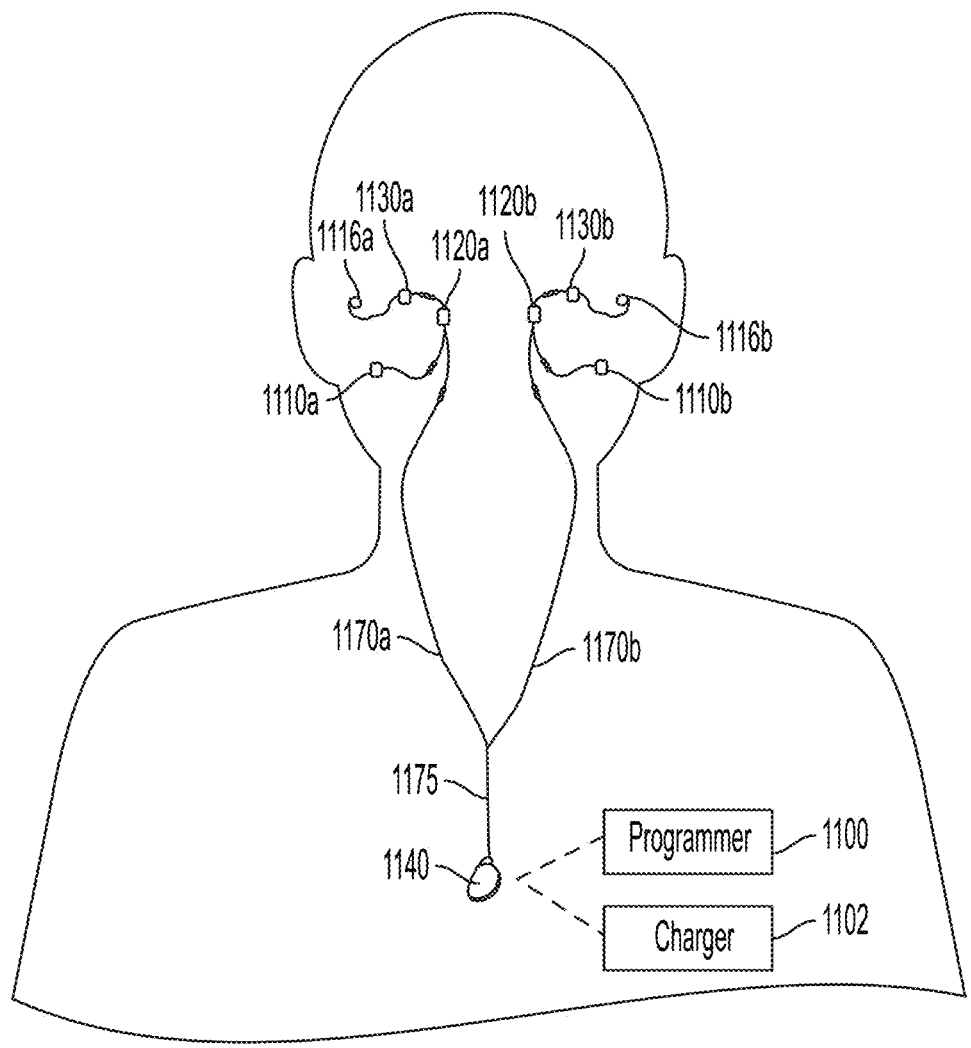
FIG. 11 shows an example embodiment wherein the cochlear implant system comprises components implanted for both sides of the wearer (e.g. for both their right ear and their left ear

FIG. 11 shows an example embodiment wherein the cochlear implant system comprises components implanted for both sides of the wearer (e.g. for both their right ear and their left ear). As shown, the cochlear implant system of FIG. 11 comprises a first subsystem comprising a first cochlear electrode 1116a, a first electrical stimulator 1130a, a first inner ear sensor 1110a, and a first signal processor 1120a, and a second subsystem comprising a second cochlear electrode 1116b, a second electrical stimulator 1130b, a second inner ear sensor 1110b, and a second signal processor 1120b. The first subsystem and the second subsystem can be configured similarly to other cochlear implant systems discussed herein. In some embodiments, the first electrical stimulator 1130a and the first signal processor 1120a can be housed in a first housing with the first cochlear electrode 1116a extending from the first housing. Additionally or alternatively, the second electrical stimulator 1130b and the second signal processor 1120b can be housed in a second housing with the second cochlear electrode 1116b extending from the second housing. Additionally or alternatively, in some embodiments, the first inner ear sensor 1110a can be included as a part of the first cochlear electrode 1116a, such as the example shown in FIG. 5. Similarly, in some embodiments, the second inner ear sensor 1110b can be included as a part of the second cochlear electrode 1116.

The cochlear implant system of FIG. 11 comprises an implantable battery and/or communication module 1140. In some embodiments, the cochlear implant system can comprise a plurality of implantable battery and/or communication modules, even though not shown in FIG. 11. The implantable battery and/or communication module 1140 can be configured to adjust a first transfer function associated with the first signal processor 1120a and adjust a second transfer function associated with the second signal processor 1120b.

In some such embodiments, the implantable battery and/or communication module 1140 can be in communication with the first signal processor 1120a via a first lead 1170a and be in communication with the second signal processor 1120b via a second lead 1170b. In some such embodiments, such as shown in FIG. 11, the first lead 1170a may be different than second lead 1170b.

Additionally or alternatively, the implantable battery and/or communication module 1140 can be in communication with both the first signal processor 1120a and the second signal processor 1120b via a bifurcated lead 1175. In some such examples, the implantable battery and/or communication module 1140 can be configured to simultaneously send an output signal to each of the first signal processor 1120a and the second signal processor 1120b via the bifurcated lead 1175. In some embodiments, the implantable battery and/or communication module 1140 provides the same output signal to both the first signal processor 1120a and the second signal processor 1120b. The implantable battery and/or communication module 1140 can be configured to communicate addressed output signals to the first signal processor 1120a and the second signal processor 1120b via the bifurcated lead 1175, wherein the addressed output signals comprises address information designating at least one of the first signal processor 1120a and the second signal processor 1120b. In some such embodiments, first signal processor 1120a and second signal processor 1120b can be configured to detect the address information and respond only to signal addressing the particular signal processor. For instance, in some examples, the first signal processor 1120a may be unaffected by an addressed output signal comprising address information designating the second signal processor 1120b and not the first signal processor 1120a. Similarly, the second signal processor 1120b may be unaffected by an addressed output signal comprising address information designating the first signal processor 1120a and not the second signal processor 1120b. Alternatively, the battery and/or communication module 1140 may communicate either the same signal or a different signal to first signal processor 1120a and second signal processor 1120b without bifurcated lead 1175, such as an embodiment having two separate outputs from the battery and/or communication module 1140.

As discussed herein, an implantable battery and/or communication module can be configured to communicate with a signal processor to adjust a transfer function associated therewith. In some examples, the implantable battery and/or communication module 1140 can be configured to adjust the first transfer function for the first signal processor 1120a, the second transfer function for the second signal processor 1120b, or a combination of the two, for example, in response to a received command. In such embodiments, the implantable battery and/or communication module 1140 may be configured to receive the commands from the external device via a wireless communication interface (e.g. Bluetooth, Wi-Fi, NFC, etc.).

In some embodiments, the cochlear implant system can receive a command to change a volume associated with the cochlear implant system. In some embodiments, the volume associated with the cochlear implant system may be an overall volume or a volume of a specific range of frequencies and/or tones (e.g. reduction of background noise, emphasis of speech, an increase of volume from one source relative to another, etc.). In some examples, the implantable battery and/or communication module 1140 can be configured to, in response to a command to change the volume, adjust a relative volume of both the first transfer function and the second transfer function by approximately the same amount.

However, in some examples, a wearer may have different amounts or types of hearing loss on one side vs the other. In such examples, increasing the volume of the first transfer function the same as the second transfer function may not correlate to a patient perceiving the same relative volume change on both sides. As such, the first transfer function and the second transfer function may be updated such that the patient perceives a similar change in output via the first electrical stimulator 1130a and the second electrical stimulator 1130b in response to a given stimulus.

In response to the command to change the volume, the implantable battery and/or communication module 1140 can be configured to determine an existing first transfer function associated with the first signal processor 1120a and determine an updated first transfer function based on the determined existing first transfer function and the received command. Additionally, the implantable battery and/or communication module 1140 can be configured to determine an existing second transfer function associated with the second signal processor 1120b and determine an updated second transfer function based on the determined existing second transfer function and the received command. In such embodiments, the updated first transfer function and the updated second transfer function may reflect a change in perceived volume as prescribed in the received command. However, the changes to the first transfer function and the second transfer function need not be the same, despite resulting from the same received command.

For instance, in some embodiments, in response to a command to change a volume, the implantable battery and/or communication module can be configured to individually change a volume associated with the first transfer function and a volume associated with the second transfer function. In some such embodiments, the adjustment to the first transfer function may reflect the same or a different adjustment than the adjustment to the second transfer function. In an example embodiment, in response to receiving a command to change the volume, the implantable battery and/or communication module can be configured to adjust the volume of the first transfer function by more or less than the second transfer function, such that a wearer perceives more or less change in the stimulation output via the first electrical stimulator 1130a than the second electrical stimulator 1130b.

Transfer functions associated with separate signal processors can be updated differently in response to a common command (e.g., "increase volume") in order to accommodate for different hearing profiles associated with each subsystem. For instance, in an example embodiment, a first subsystem and a second subsystem can be programmed with different transfer functions based on, for example, the wearer's hearing profile in the left and right ears, the operation of an inner ear sensor in each of the first and second subsystems (which might behave differently based on, for example, a wearer's anatomy), and the like. A command to "increase volume" might result in different adjustments to the different transfer functions. For example, a first transfer function might increase a gain by 10% while the second transfer function might increase a gain by 20% in one or more frequency ranges. Each change can be determined, for example, based on a prescribed response to a given command based on an existing transfer function.

In some embodiments, systems including two different subsystems, such as shown in FIG. 11, can be used to perform various functions described herein, such as detecting a stapedial reflex in a wearer. In an example embodiment, an acoustic stimulus can be provided to a first ear of the wearer, such as via an in-ear speaker (e.g., in communication with a fitting hub). The acoustic stimulus can be detected via first inner ear sensor 1110, which can provide an input signal to the first signal processor 1120a programmed with a first transfer function and output a corresponding stimulation signal to the first electrical stimulator 1130a. The first electrical stimulator 1130a can provide an electrical stimulus to the wearer's cochlear tissue based on the stimulation signal.

The implantable battery and/or communication module 1140 can receive information from the second signal processor 1120b representing data received from the second inner ear sensor 1110b. Generally, a stapedial reflex occurs in the inner ear of both sides of a person, even if the stimulus is applied to only a single ear. Accordingly, the implantable battery and/or communication module 1140 can be configured to detect a stapedial reflex triggered in the wearer based on the information received from the second signal processor 1120b in response to the stimulus detected by the first inner ear sensor 1110a.

In some embodiments, this phenomenon can be leveraged in order to perform various stapedial reflex processes described herein. For example, a fitting hub can provide a stimulus of increasing intensity to a first ear of a wearer until the implantable battery and/or communication module detects a stapedial reflex in the other ear of the wearer. Similar to described elsewhere herein, the intensity the sound that triggered the stapedial reflex can be used to calibrate the transfer function of the signal processor associated with the sensor used in the first ear. Such a process can be repeated for a plurality of frequencies and for the other ear.

Various non-limiting embodiments have been described. These and others are within the scope of the following claims.

The invention claimed is:
1. A cochlear implant system comprising:
a first subsystem including:
a first cochlear electrode;
a first stimulator in electrical communication with the first cochlear electrode;
a first inner ear sensor configured to receive a stimulus signal from surrounding cochlear tissue and/or fluid of a wearer and generate a first input signal based on the received stimulus signal; and
a first signal processor in communication with the first stimulator and the first inner ear sensor, the first signal processor being programmed with a first transfer function and being configured to:
receive the first input signal from the first inner ear sensor; and
output a first stimulation signal to the first stimulator based on the received first input signal and the first transfer function to cause the first stimulator to output first electrical signals to the first cochlear electrode;
a second subsystem including:
a second cochlear electrode;
a second stimulator in communication with the second cochlear electrode;
a second input source configured to receive a second stimulus signal and generate a second input signal based on the received second stimulus signal; and
a second signal processor in communication with the second stimulator and the second input source, the second signal processor programmed with a second transfer function and being configured to:
receive the second input signal from the second input source; and
output a second stimulation signal to the second stimulator based on the second input signal and the second transfer function to cause the second stimulator to output second electrical signals to the second cochlear electrode; and
an implantable module comprising an implantable battery and/or an implantable communication module in communication with the first signal processor and the second signal processor and configured to provide electrical power to the first signal processor and the second signal processor.

2. The cochlear implant system of claim 1, wherein first the cochlear electrode comprises a plurality of contact electrodes configured to receive electrical signals from the first stimulator; and wherein the first inner ear sensor is included as a part of the first cochlear electrode.

3. The cochlear implant system of claim 2, wherein the first inner ear sensor comprises a pressure sensor, and wherein the received stimulus signal comprises a measured pressure.

4. The cochlear implant system of claim 2, comprising a housing; and wherein the first signal processor and the first stimulator are included in the housing, and wherein the first cochlear electrode including the first inner ear sensor extends from the housing.

5. The cochlear implant system of claim 1, further comprising:
an external hub including a speaker and a wireless communication interface, the external hub being configured to communicate wirelessly with the implantable module, the external hub being configured to output a first predetermined acoustic signal via the speaker and communicate information regarding the first predetermined acoustic signal to the implantable module via the wireless communication interface.

6. The cochlear implant system of claim 5, wherein, in response to the external hub outputting the first predetermined acoustic signal via the speaker:
the first inner ear sensor receives a stimulus resulting from the first predetermined acoustic signal and generates the first input signal in response thereto;
the first signal processor receives the first input signal from the first inner ear sensor and communicates information representative of the received first input signal to the implantable module; and wherein the system is configured to:
receive information from the external hub regarding the first predetermined acoustic signal output from the speaker of the external hub;
analyze the information received from the external hub regarding the output first predetermined acoustic signal and the information received from the first signal processor representative of the received first input signal to determine a relationship between the first predetermined acoustic signal output from the speaker of the external hub and the resulting first input signal generated via the first inner ear sensor.

7. The cochlear implant system of claim 6, wherein the system is further configured to update the transfer function of the first signal processor in response to the determined relationship.

8. The cochlear implant system of claim 6, wherein
the external hub is configured to output a plurality of predetermined acoustic signals including the first predetermined acoustic signal; and
for each of the output predetermined acoustic signals, the system is configured to:
receive information from the external hub regarding the acoustic signal output from the speaker of the external hub; and
analyze information received from the external hub regarding the output predetermined acoustic signal and information received from the first signal processor representative of the received first input signal to determine the relationship between the predetermined acoustic signal output from the speaker of the external hub and the resulting first input signal generated via the first inner ear sensor.

9. The cochlear implant system of claim 8, wherein the each of the plurality of predetermined acoustic signals comprises a different one of a plurality of frequencies and each of the plurality of predetermined acoustic signals comprise substantially the same intensity.

10. The cochlear implant system of claim 1, comprising a first housing and a second housing; and wherein
the first stimulator and the first signal processor are housed in the first housing;
the first cochlear electrode extends from the first housing;
the second stimulator and the second signal processor are housed in the second housing; and
the second cochlear electrode extends from the second housing.

11. The cochlear implant system of claim 1, wherein the implantable module is configured to adjust the first transfer function associated with the first signal processor and to adjust the second transfer function associated with the second signal processor.

12. The cochlear implant system of claim 11, further comprising a bifurcated lead and wherein the implantable module is in communication with both the first signal processor and the second signal processor via the bifurcated lead; and wherein
the implantable module sends the same signals to each of the first signal processor and the second signal processor via the bifurcated lead and
the implantable module is configured to communicate addressed output signals to the first signal processor and the second signal processor via the bifurcated lead, the addressed output signals comprising address information designating at least one of the first signal processor and the second signal processor.

13. The cochlear implant system of claim 11, wherein the implantable module comprises a wireless communication interface and is configured to receive a command to adjust the first transfer function and the second transfer function from an external device via the wireless communication interface.

14. The cochlear implant system of claim 13, wherein the implantable module is configured to:
adjust the first transfer function based on the received command and the first transfer function; and
adjust the second transfer function based on the received command and the second transfer function; such that
adjusting the first transfer function is independent of adjusting the second transfer function.

15. The cochlear implant system of claim 14, wherein:
the received command comprises a command to change a volume associated with the cochlear implant system; and
in response to the received command, the implantable module is configured to:
determine an existing first transfer function associated with the first signal processor;
determine an updated first transfer function based on the determined existing first transfer function and the received command reflecting a change in perceived volume with respect to the existing first transfer function as prescribed in the received command;
determine an existing second transfer function associated with the second signal processor;
determine an updated second transfer function based on the determined existing second transfer function and the received command reflecting a change in perceived volume with respect to the existing second transfer function as prescribed in the received command.

16. The cochlear implant system of claim 1, wherein the second cochlear electrode comprises a plurality of contact electrodes configured to receive electrical signals from the second stimulator; and wherein the second input source comprises a second inner ear sensor included as a part of the second cochlear electrode.

17. The cochlear implant system of claim 1, comprising a first lead and a second lead, and wherein:
the implantable module is in communication with the first signal processor via the first lead;
the implantable module is in communication with the second signal processor via the second lead;
the implantable module is configured to adjust the first transfer function via communication with the first signal processor via the first lead; and
the implantable module is configured to adjust the second transfer function via communication with the second signal processor via the second lead.

18. A cochlear implant system comprising:
a cochlear electrode;
a stimulator in electrical communication with the cochlear electrode;
an inner ear sensor configured to receive a stimulus signal from surrounding cochlear tissue and/or fluid of a wearer and generate an input signal based on the received stimulus signal; and
a signal processor in communication with the stimulator and the inner ear sensor, the signal processor being programmed with a transfer function and being configured to:
receive the input signal from the inner ear sensor; and
output a stimulation signal to the stimulator based on the received input signal and the transfer function to cause the stimulator to output electrical signals to the cochlear electrode;
an implantable module comprising an implantable battery and/or an implantable communication module in communication with the signal processor and being configured to provide electrical power to the signal processor; and an external hub including a speaker and a wireless communication interface, the external hub being configured to communicate wirelessly with the implantable module, the external hub being configured to output a first predetermined acoustic signal via the speaker and communicate information regarding the first predetermined acoustic signal to the implantable module via the wireless communication interface.

19. The cochlear implant system of claim 18, wherein, in response to the external hub outputting the first predetermined acoustic signal via the speaker:
the inner ear sensor receives a stimulus resulting from the first predetermined acoustic signal and generates the input signal in response thereto;
the signal processor receives the input signal from the inner ear sensor and communicates information representative of the received input signal to the implantable module; and wherein the system is configured to:
receive information from the external hub regarding the acoustic signal output from the speaker of the external hub;
analyze the information received from the external hub regarding the output first predetermined acoustic signal and the information received from the signal processor representative of the received input signal to determine a relationship between the first predetermined acoustic signal output from the speaker of the external hub and the resulting input signal generated via the inner ear sensor.

20. The cochlear implant system of claim 19, wherein the system is further configured to update the transfer function of the signal processor in response to the determined relationship.

21. The cochlear implant system of claim 19, wherein
the external hub is configured to output a plurality of predetermined acoustic signals including the first predetermined acoustic signal; and
for each of the output predetermined acoustic signals, the system is configured to:
receive information from the external hub regarding the acoustic signal output from the speaker of the external hub; and
analyze information received from the external hub regarding the output predetermined acoustic signal and information received from the signal processor representative of the received input signal to determine the relationship between the predetermined acoustic signal output from the speaker of the external hub and the resulting input signal generated via the inner ear sensor.

22. The cochlear implant system of claim 21, wherein the each of the plurality of predetermined acoustic signals comprises a different one of a plurality of frequencies and each of the plurality of predetermined acoustic signals comprise substantially the same intensity.

23. The cochlear implant system of claim 18, wherein the cochlear electrode comprises a plurality of contact electrodes configured to receive electrical signals from the stimulator; and wherein the inner ear sensor is included as a part of the cochlear electrode.

24. The cochlear implant system of claim 23, wherein the inner ear sensor comprises a pressure sensor, and wherein the received stimulus signal comprises a measured pressure.

* * * * *